US012434056B2

(12) United States Patent
Duran et al.

(10) Patent No.: US 12,434,056 B2
(45) Date of Patent: Oct. 7, 2025

(54) BILATERALLY-COORDINATED CHANNEL SELECTION

(71) Applicant: Cochlear Limited, Macquarie University (AU)

(72) Inventors: Sara Ingrid Duran, Macquarie University (AU); Zachary Mark Smith, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 1245 days.

(21) Appl. No.: 17/261,231

(22) PCT Filed: Sep. 6, 2019

(86) PCT No.: PCT/IB2019/057536
§ 371 (c)(1),
(2) Date: Jan. 19, 2021

(87) PCT Pub. No.: WO2020/053726
PCT Pub. Date: Mar. 19, 2020

(65) Prior Publication Data

US 2021/0268282 A1 Sep. 2, 2021

Related U.S. Application Data

(60) Provisional application No. 62/730,685, filed on Sep. 13, 2018.

(51) Int. Cl.
*A61N 1/36* (2006.01)
*H04R 25/00* (2006.01)

(52) U.S. Cl.
CPC ....... *A61N 1/36039* (2017.08); *H04R 25/505* (2013.01); *H04R 25/552* (2013.01);
(Continued)

(58) Field of Classification Search
CPC ............ A61N 1/36038; A61N 1/36039; H04R 2460/01; H04R 25/43; H04R 25/505; H04R 25/552; H04R 25/554; H04R 25/70
See application file for complete search history.

(56) References Cited

U.S. PATENT DOCUMENTS 5,597,380 A 1/1997 McDermott et al.
7,937,155 B1 5/2011 Voelkel et al.
(Continued)

FOREIGN PATENT DOCUMENTS

WO 2012084026 A1 6/2012
WO 2018085620 A1 5/2018

OTHER PUBLICATIONS

International Search Report and the Written Opinion, PCT/IB2019/057536, Jan. 7, 2018, 13 pages.
(Continued)

*Primary Examiner* — Amanda K Hulbert
(74) *Attorney, Agent, or Firm* — Edell, Shapiro & Finnan, LLC

(57) ABSTRACT

Presented herein are techniques for bilateral-coordination of channel selection in bilateral hearing prosthesis systems. A bilateral hearing prosthesis system comprises first and second hearing prostheses each configured to receive sound signals, and a processing module. The processing module is configured to select, based on bilateral sound information, a set of sound processing channels for use by both of the first and second hearing prostheses. The first hearing prosthesis is configured stimulate the first ear of the recipient using stimulation generated from the sound signals received at the first hearing prosthesis and processed in at least the set of sound processing channels by the first hearing prosthesis. The second hearing prosthesis is configured stimulate the second ear of the recipient using stimulation generated from the sound signals received at the second hearing prosthesis
(Continued)

and processed in at least the set of sound processing channels by the second hearing prosthesis.

29 Claims, 20 Drawing Sheets

(52) U.S. Cl.
CPC ........... *H04R 25/554* (2013.01); *H04R 25/70* (2013.01); *H04R 25/43* (2013.01)

(56) References Cited

U.S. PATENT DOCUMENTS 9,713,715 B2 7/2017 Smith
2011/0125218 A1* 5/2011 Busby ................ A61N 1/36038 607/57
2013/0023963 A1 1/2013 Stafford et al.
2014/0219486 A1* 8/2014 Brown ................. H04R 25/505 381/320
2016/0367805 A1* 12/2016 Dietz ................ A61N 1/36039
2017/0347213 A1 11/2017 Goorevich et al.

OTHER PUBLICATIONS

Kelvasa et al., "Auditory Model-Based Sound Direction Estimation With Bilateral Cochlear Implants" Trends in Hearing, 2015, vol. 19: 17 pages.
Wang et al., "Cooperating Speech Processing Strategy and Pitch Mismatch in Bilateral Cochlear Implants: Predictions from an Acoustic Model", Duke University, 1 page.

* cited by examiner

1450

FIG. 18A
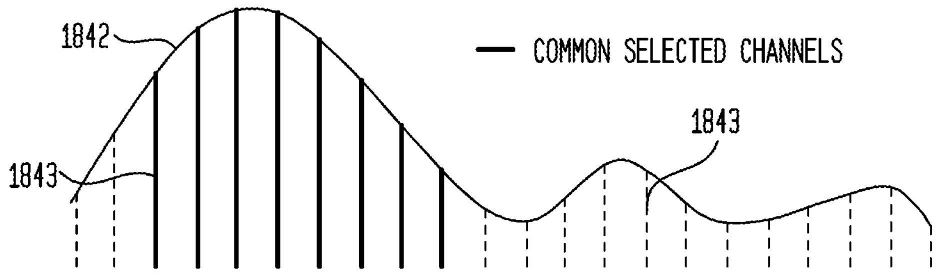
| | | | | | | | | | | | | | | | | | | | | | |
|---|---|---|---|---|---|---|---|---|---|---|---|---|---|---|---|---|---|---|---|---|---|
| CHANNEL NUMBER | 22 | 21 | 20 | 19 | 18 | 17 | 16 | 15 | 14 | 13 | 12 | 11 | 10 | 9 | 8 | 7 | 6 | 5 | 4 | 3 | 2 | 1 |
| CHANNEL RANK(R) | 16 | 7 | 5 | 3 | 1 | 2 | 4 | 6 | 8 | 11 | 18 | 21 | 14 | 9 | 10 | 15 | 20 | 19 | 17 | 13 | 12 | 22 |
FIG. 18B
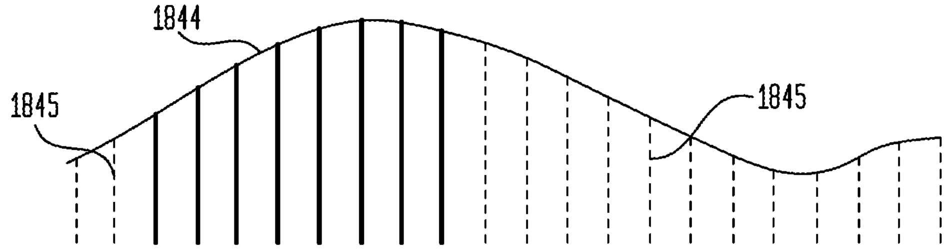
| | | | | | | | | | | | | | | | | | | | | | |
|---|---|---|---|---|---|---|---|---|---|---|---|---|---|---|---|---|---|---|---|---|---|
| CHANNEL NUMBER | 22 | 21 | 20 | 19 | 18 | 17 | 16 | 15 | 14 | 13 | 12 | 11 | 10 | 9 | 8 | 7 | 6 | 5 | 4 | 3 | 2 | 1 |
| CHANNEL RANK(L) | 20 | 14 | 12 | 10 | 8 | 6 | 4 | 1 | 2 | 3 | 5 | 7 | 9 | 11 | 13 | 16 | 18 | 21 | 22 | 19 | 17 | 15 |
FIG. 18C
| | | | | | | | | | | | | | | | | | | | | | |
|---|---|---|---|---|---|---|---|---|---|---|---|---|---|---|---|---|---|---|---|---|---|
| CHANNEL NUMBER | 22 | 21 | 20 | 19 | 18 | 17 | 16 | 15 | 14 | 13 | 12 | 11 | 10 | 9 | 8 | 7 | 6 | 5 | 4 | 3 | 2 | 1 |
| SUMMED RANK(R+L) | 36 | 21 | **17** | **13** | **9** | **8** | **8** | **7** | **10** | **14** | 23 | 28 | 23 | 20 | 33 | 31 | 38 | 40 | 39 | 32 | 29 | 37 |

FIG. 19A
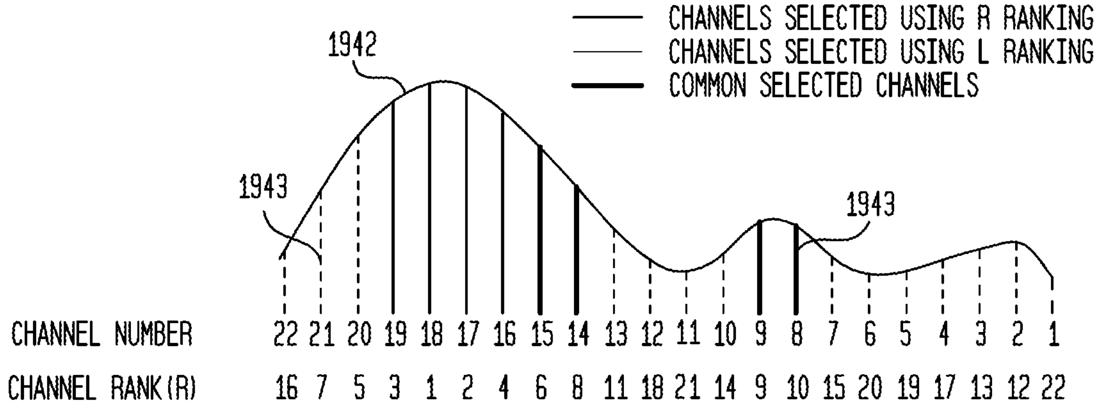
FIG. 19B
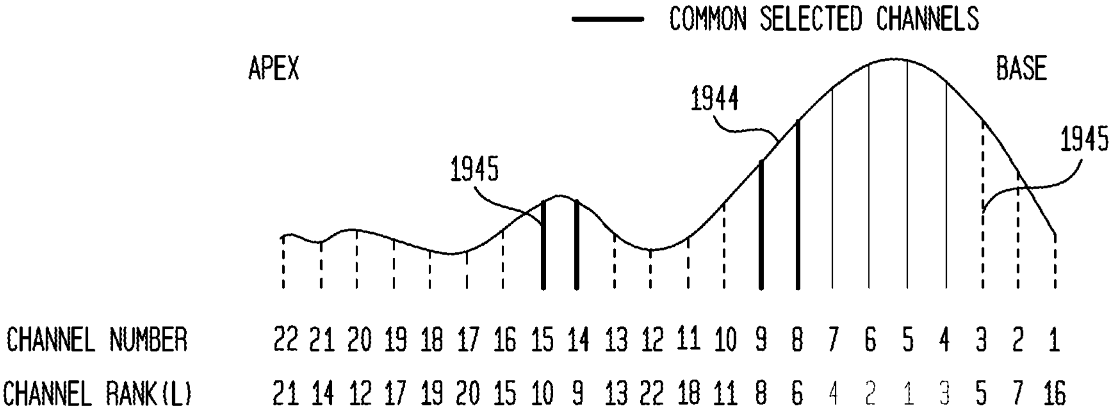
FIG. 19C
| | | | | | | | | | | | | | | | | | | | | | |
|---|---|---|---|---|---|---|---|---|---|---|---|---|---|---|---|---|---|---|---|---|---|
| CHANNEL NUMBER | 22 | 21 | 20 | 19 | 18 | 17 | 16 | 15 | 14 | 13 | 12 | 11 | 10 | 9 | 8 | 7 | 6 | 5 | 4 | 3 | 2 | 1 |
| SUMMED RANK(R+L) | 38 | 21 | 18 | 20 | 20 | 22 | 19 | **16** | **17** | 25 | 40 | 39 | 25 | **17** | **16** | 19 | 22 | 20 | 20 | 18 | 19 | 38 |

2050

BILATERALLY-COORDINATED CHANNEL SELECTION

BACKGROUND

Field of the Invention

The present invention relates generally to coordinated channel selection in a bilateral hearing prosthesis system.

Related Art

Medical device systems have provided a wide range of therapeutic benefits to recipients over recent decades. For example, a hearing prosthesis system is a type of medical device system that includes one or more hearing prostheses that operate to convert sound signals into one or more acoustic, mechanical, and/or electrical stimulation signals for delivery to a recipient. The one or more hearing prostheses that can form part of a hearing prosthesis system include, for example, hearing aids, cochlear implants, middle ear stimulators, bone conduction devices, brain stem implants, electro-acoustic devices, and other devices providing acoustic, mechanical, and/or electrical stimulation to a recipient.

One specific type of hearing prosthesis system, referred to herein as a "bilateral hearing prosthesis system" or more simply as a "bilateral system," includes two hearing prostheses, positioned at each ear of the recipient. More specifically, in a bilateral system each of the two prostheses provides stimulation to one of the two ears of the recipient (i.e., either the right or the left ear of the recipient). Bilateral systems can improve the recipient's perception of sound signals by, for example, eliminating the head shadow effect, leveraging interaural time delays and level differences that provide cues as to the location of the sound source and assist in separating desired sounds from background noise, etc.

SUMMARY

In one aspect presented herein, a method is provided. The method comprises: receiving sound signals at first and second hearing prostheses in a bilateral hearing prosthesis system; obtaining, at a processing module of the bilateral hearing prosthesis system, bilateral sound information, wherein the bilateral sound information comprises information associated with the sound signals received at each of the first and second hearing prostheses; at the processing module, selecting a set of sound processing channels for use by both of the first and second hearing prostheses in stimulating first and second ears, respectively, of the recipient; at the first hearing prosthesis, stimulating the first ear of the recipient using stimulation generated from the sound signals received at the first hearing prosthesis and processed in at least the set of sound processing channels by the first hearing prosthesis; and at the second hearing prosthesis, stimulating the second ear of the recipient using stimulation generated from the sound signals received at the second hearing prosthesis and processed in at least the set of sound processing channels by the second hearing prosthesis.

BRIEF DESCRIPTION OF THE DRAWINGS

Embodiments of the present invention are described herein in conjunction with the accompanying drawings, in which:

FIGS. 18A, 18B and 18C are graphs illustrating one example implementation of the bilaterally-coordinated channel selection method of FIG. 17;

FIGS. 19A, 19B and 19C are graphs illustrating an alternative implementation of a bilaterally-coordinated channel selection method of FIG. 17;

DETAILED DESCRIPTION

Presented herein are techniques for bilateral-coordination of channel selection in bilateral hearing prosthesis systems. A bilateral hearing prosthesis system comprises first and second hearing prostheses each configured to receive sound signals, as well as a processing module. The processing module is configured to select, based on bilateral sound information, a set of sound processing channels for use by both of the first and second hearing prostheses. The first hearing prosthesis is configured stimulate the first ear of the recipient using stimulation generated from the sound signals received at the first hearing prosthesis and processed in at least the set of sound processing channels by the first hearing prosthesis. The second hearing prosthesis is configured stimulate the second ear of the recipient using stimulation generated from the sound signals received at the second hearing prosthesis and processed in at least the set of sound processing channels by the second hearing prosthesis.

For ease of illustration, the techniques presented herein will primarily be described with reference to a particular illustrative bilateral hearing prosthesis system, namely a bilateral cochlear implant system. However, it is to be appreciated that the techniques presented herein may be used in other bilateral hearing prosthesis systems, such as bimodal systems, bilateral hearing prosthesis systems including auditory brainstem stimulators, hearing aids, bone conduction devices, mechanical stimulators, etc. Accordingly, it is to be appreciated that the specific implementations described below are merely illustrative and do not limit the scope of the techniques presented herein.

Figure 1A:
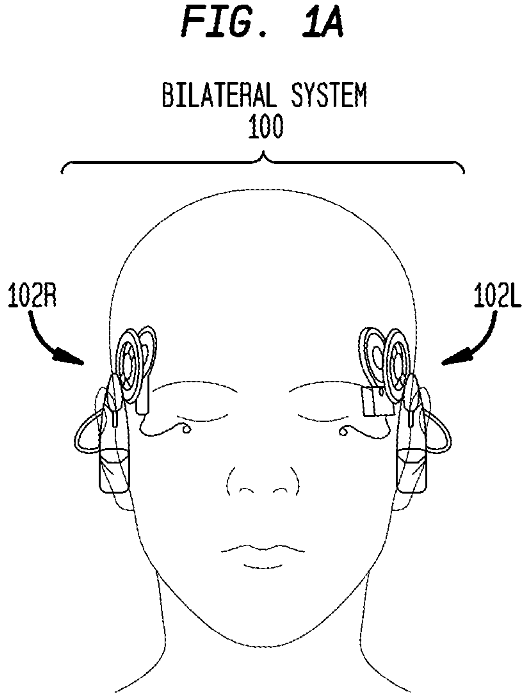
FIG. 1A is a schematic view of a bilateral hearing prosthesis system in which embodiments of presented herein may be implemented.
Figure 1B:
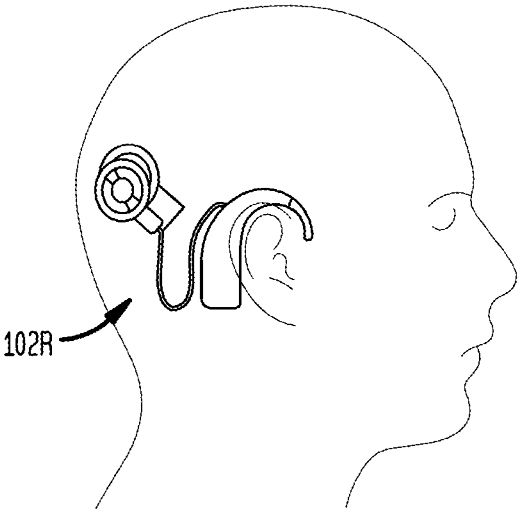
FIG. 1B is a side view of a recipient including the bilateral hearing prosthesis system of FIG. 1A.
Figure 2:
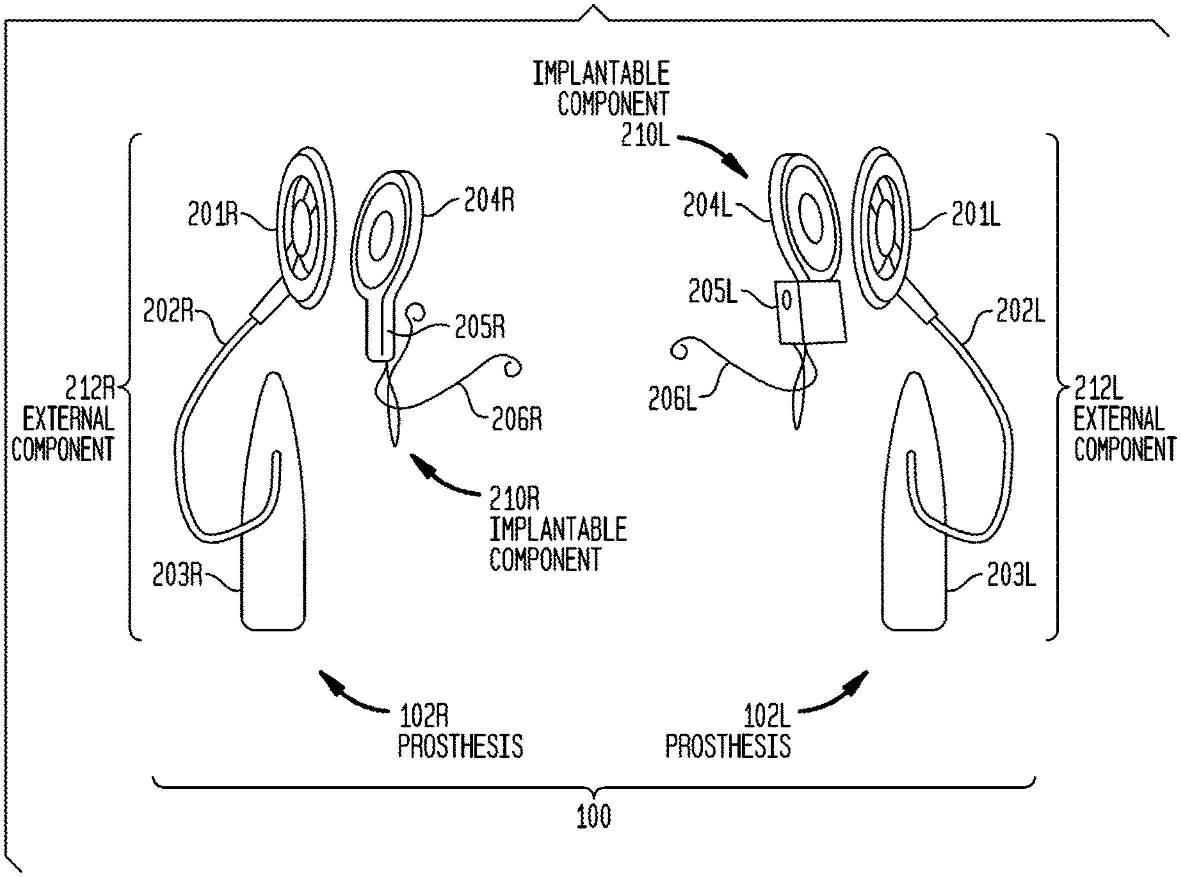
FIG. 2 is a schematic view of the components of the bilateral hearing prosthesis system of FIG. 1A.

FIGS. 1A and 1B are schematic drawings of a recipient wearing a left cochlear prosthesis 102L and a right cochlear prosthesis 102R, collectively referred to as "bilateral prostheses" that are part of a bilateral cochlear implant system (bilateral system) 100. FIG. 2 is a schematic view of bilateral system 100 of FIGS. 1A and 1B. As shown in FIG. 2, prosthesis 102L includes an external component 212L comprising a sound processing unit 203L electrically connected to an external coil 201L via cable 202L.

Prosthesis 102L also includes implantable component 210L implanted in the recipient. Implantable component 210L includes an internal coil 204L, a stimulator unit 205L and a stimulating assembly (e.g., electrode array) 206L implanted in the recipient's left cochlea (not shown in FIG. 2). In operation, a sound received by prosthesis 102L is converted to an encoded data signal by a sound processor within sound processing unit 203L, and is transmitted from external coil 201L to internal coil 204L via, for example, a magnetic inductive radio frequency (RF) link. This link, referred to herein as a Closely Coupled Link (CCL), is also used to transmit power from external component 212L to implantable component 210L.

In the example of FIG. 2, prosthesis 102R is substantially similar to prosthesis 102L. In particular, prosthesis 102R includes an external component 212R comprising a sound processing unit 203R, a cable 202R, and an external coil 201R. Prosthesis 102R also includes an implantable component 210R comprising internal coil 204R, stimulator 205R, and stimulating assembly 206R.

Figure 3:
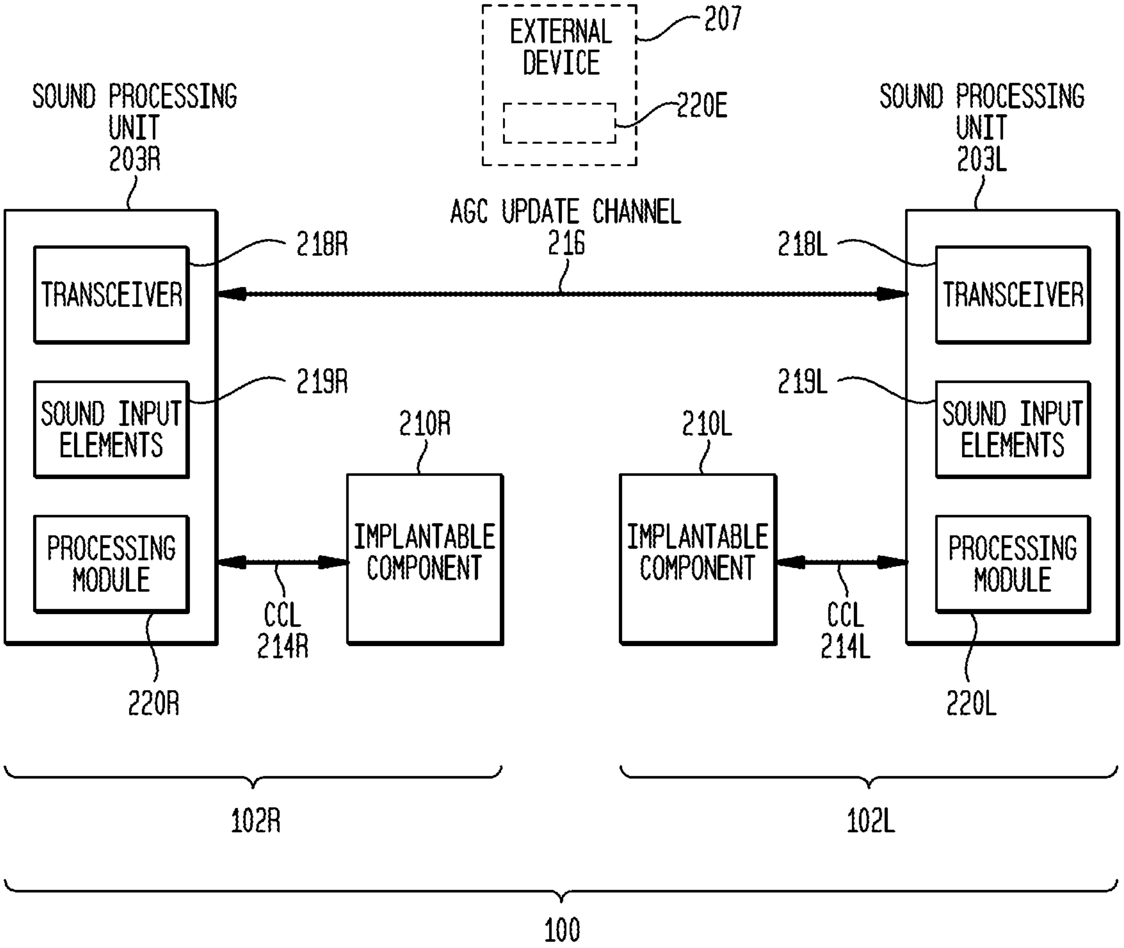
FIG. 3 is a simplified block diagram of selected components of the bilateral hearing prosthesis system of FIG. 1A.

FIG. 3 is a schematic diagram that functionally illustrates selected components of bilateral system 100, as well as the communication links implemented therein. As noted, bilateral system 100 comprises sound processing units 203L and 203R. The sound processing unit 203L comprises a transceiver 218L, one or more sound input elements (e.g., microphones) 219L, and a processing module 220L. Similarly, sound processing unit 203R also comprises a transceiver 218R, one or more sound input elements (e.g., microphones) 219R, and a processing module 220R.

Sound processor 203L communicates with an implantable component 210L via a CCL 214L, while sound processor 203R communicates with implantable component 210R via CCL 214R. In one embodiment, CCLs 214L and 214R are magnetic induction (MI) links, but, in alternative embodiments, links 214L and 214R may be any type of wireless link now know or later developed. In the exemplary arrangement of FIG. 3, CCLs 214L and 214R generally operate (e.g., purposefully transmit data) at a frequency in the range of about 5 to 50 MHz.

As shown in FIG. 3, sound processing units 203L and 203R use the transceiver 218L and 218R to communicate with one another via a separate bilateral wireless channel or link 216. The bilateral link 216 may be, for example, a magnetic inductive (MI) link, a short-range wireless link, such as a Bluetooth® link that communicates using short-wavelength Ultra High Frequency (UHF) radio waves in the industrial, scientific and medical (ISM) band from 2.4 to 2.485 gigahertz (GHz), or another type of wireless link. Bluetooth® is a registered trademark owned by the Bluetooth® SIG. As described further below, in accordance with certain embodiments presented herein, the bilateral link 216 is used to exchange bilateral sound information between the sound processing units 203L and 203R. Although FIGS. 1A, 1B, 2, and 3 generally illustrate the use of wireless communications between the bilateral prostheses 102L and 102R, it is to be appreciated that the embodiments presented herein may also be implemented in systems that use a wired bilateral channel.

FIGS. 1A, 1B, 2, and 3 generally illustrate an arrangement in which the bilateral system 100 includes external components located at the left and right ears of a recipient. It is to be appreciated that embodiments of the present invention may be implemented in bilateral systems having alternative arrangements. For example, embodiments of the present invention can also be implemented in a totally implantable bilateral system. In a totally implantable bilateral system, all components are configured to be implanted under skin/tissue of a recipient and, as such, the system operates for at least a finite period of time without the need of any external devices.

As noted above, the cochlear prostheses 102L and 102R include a sound processing unit 203L and 203R, respectively. These sound processing unit 203L and 203 include processing modules 220R and 220L, respectively. The processing modules 220R and 220L may be formed by one or more processors (e.g., one or more Digital Signal Processors (DSPs), one or more uC cores, etc.), firmware, software in memory (e.g., non-volatile memory, program memory, etc.) and executed by one or more processors, etc. arranged to perform the operations described herein.

The processing modules 220R and 220L are each configured to perform one or more sound processing operations to convert sound signals into stimulation control signals that are useable by a stimulator unit to generate electrical stimulation signals for delivery to the recipient. These sound processing operations generally include channel selection operations. More specifically, a recipient's cochlea is tonotopically mapped, that is, partitioned into regions each responsive to sound signals in a particular frequency range. In general, the basal region of the cochlea is responsive to higher frequency sounds, while the more apical regions of the cochlea are responsive to lower frequency sounds. The tonotopic nature of the cochlea is leveraged in cochlear implants such that specific acoustic frequencies are allocated to the electrodes that are positioned closest to the corresponding tonotopic region of the cochlea (i.e., the region of the cochlea that would naturally be stimulated in acoustic hearing by the acoustic frequency). That is, in a cochlear implant, received sound signals are segregated/separated into bandwidth limited frequency bands/bins, sometimes referred to herein as "sound processing channel," or simply "channels," that each includes a spectral component of the received sound signals. The signals in each of these different channels are mapped to a different set of one or more electrodes that are, in turn, used to deliver stimulation signals to a selected (target) population of cochlea nerve cells (i.e., the tonotopic region of the cochlea associated with the frequency band).

The total number of sound processing channels generated and used to process the sound signals at a given time instant can be referred to as a total of "M" channels. In general, all of these M channels are not use to generate stimulation for delivery to a recipient. Instead, a subset of these channels, referred to as "N" channels, may be selected and the spectral component therein are used to generate the stimulation signals that are delivered to the recipient. Stated differently, the cochlear implant will stimulate the ear of the recipient using stimulation signals that are generated from the sound signals processed in the N selected channels. The process for selecting the N channels is referred to as "channel selection" or an "N-of-M sound coding strategy."

In conventional bilateral hearing prosthesis systems, the channel selection process is performed independently for each sound processing unit (i.e., the left side sound processing unit selects its own N channels independently from the right side sound processing unit, and vice versa). This independent/uncoordinated channel selection at each of the bilateral hearing prostheses could negatively impact recipients' perception in a number of different ways. For instance, in an extreme case the set of N channels selected by one sound processing unit could include none of the channels selected by the other sound processing unit. In this case, channel-specific interaural level differences (ILDs) could be infinite, which would negatively impact the recipient's spatial perception of the acoustic scene. Uncoordinated channel selection could also result in problems in asymmetric listening environments, where the target sound is off to one side yet the channel selected at each sound processing unit are presented to the recipient with equal weight.

Therefore, to address the above and other problems in conventional arrangements, presented herein are bilaterally-coordinated channel selection techniques in which the channel selection occurs using "bilateral sound information" generated by both of the left and right hearing prostheses. As used herein, the "bilateral sound information" is information/data associated with the sound signals received at the left hearing prosthesis and information associated with the sound signals received at the right hearing prostheses. The bilateral sound information may comprise the received sound signals (i.e., the full audio signals received at each of the left and right prostheses) or data representing one or more attributes of the received sound signals. Before further describing the bilaterally-coordinated channel selection techniques, further details of sound processing units 203R and 203L, which are configured to implement these techniques, are provided below with reference to FIG. 4.

Figure 4:
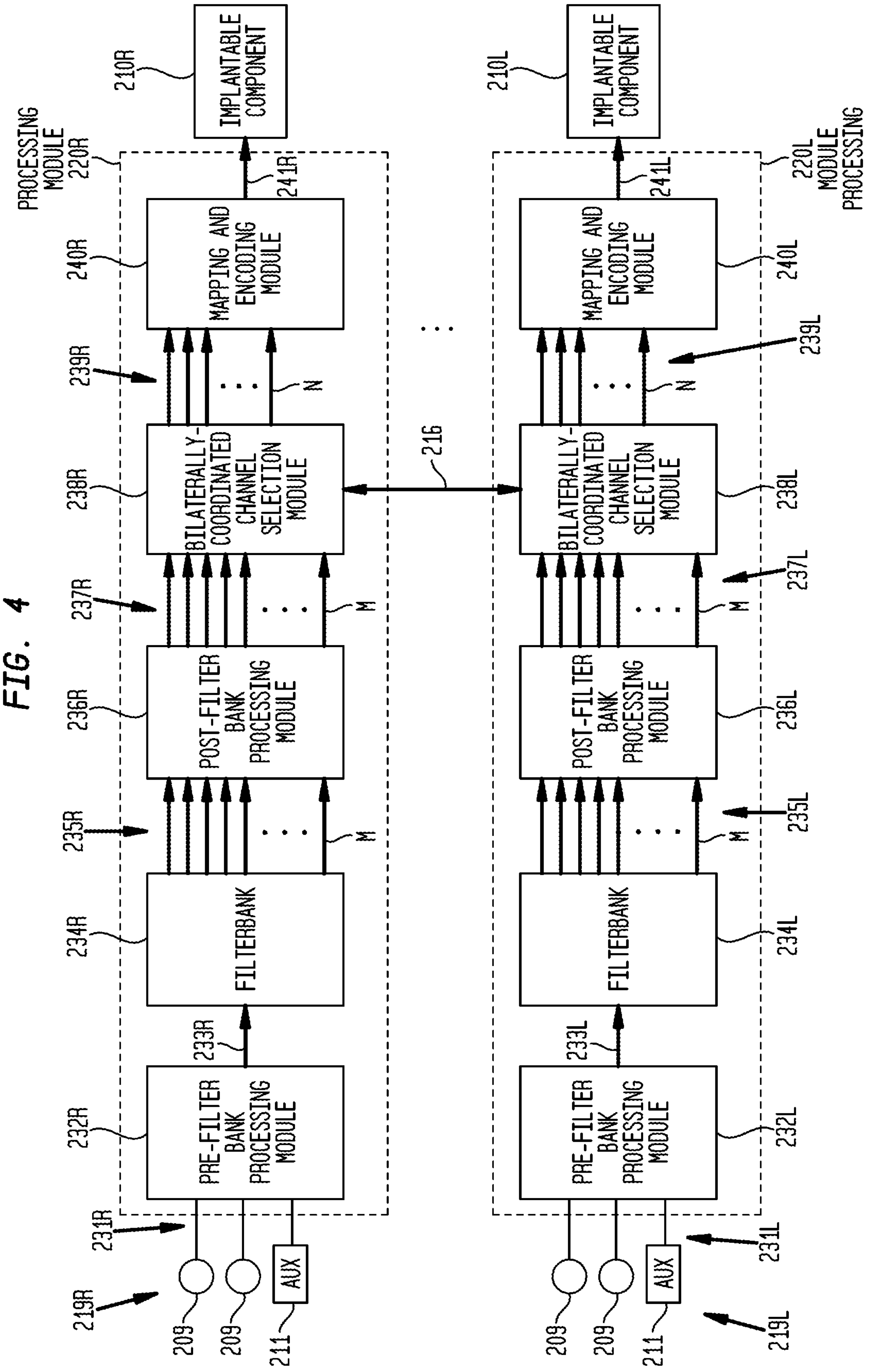
FIG. 4 is a functional block diagram of selected components of the bilateral hearing prosthesis system of FIG. 1A.

More specifically, FIG. 4 is a functional block diagram illustrating processing blocks for each of the processing module 220R and 220L of the sound processing units 203R and 203L, respectively. The processing module 220R comprises a pre-filterbank processing module 232R, a filterbank 234R, a post-filterbank processing module 236R, a bilaterally-coordinated channel selection module 238R, and a mapping and encoding module 240R. Collectively, the filterbank 234R, the post-filterbank processing module 236R, the bilaterally-coordinated channel selection module 238R, and the mapping and encoding module 240R form a right-side sound processing path that, as described further below, converts one or more sound signals into one or more output signals for use in compensation of a hearing loss of a recipient of the cochlear implant (i.e., output signals for use in generating electrical stimulation signals for delivery to a right-side cochlea of the recipient as to evoke perception of the received sound signals). The sound signals processed in the right-side sound processing path are received at one or more of the sound input elements 219R, which in this example include two (2) microphones 209 and at least one auxiliary input 211 (e.g., an audio input port, cable port, telecoil, etc.).

Processing module 220L includes similar processing blocks as those in processing module 220R, including a pre-filterbank processing module 232L, a filterbank 234L, a post-filterbank processing module 236L, a bilaterally-coordinated channel selection module 238L, and a mapping and encoding module 240L, which collectively, form a left-side sound processing path. The left-side sound processing path converts one or more sound signals into one or more output signals for use in generating electrical stimulation signals for delivery to a left-side cochlea of the recipient as to evoke perception of the received sound signals. The sound signals processed in the left-side sound processing path are received at one or more of the sound input elements 21LR, which in this example includes two (2) microphones 209 and an auxiliary input 211.

It is to be appreciated that the components of the processing module 220L, including the pre-filterbank processing module 232L, filterbank 234L, post-filterbank processing module 236L, and mapping and encoding module 240L, each operate similar to the same components of processing module 220R. As such, for ease of description, further details of the pre-filterbank processing modules, filterbanks, post-filterbank processing modules, and mapping and encoding modules will generally be described with specific reference to processing module 220R. However, as described further below, the bilaterally-coordinated channel selection techniques presented herein may be implemented differently at each of the bilaterally-coordinated channel selection modules 238R and 238L. As such, the following description will refer to both of the bilaterally-coordinated channel selection modules 238R and 238L for explanation of the bilaterally-coordinated channel selection techniques.

Referring specifically to processing module 220R, sound input elements 219R receive/detect sound signals which are then provided to the pre-filterbank processing module 232R. If not already in an electrical form, sound input elements 219R convert the sound signals into an electrical form for use by the pre-filterbank processing module 232R. The arrows 231R represent the electrical input signals provided to the pre-filterbank processing module 232R.

The pre-filterbank processing module 232R is configured to, as needed, combine the electrical input signals received from the sound input elements 219R and prepare those signals for subsequent processing. The pre-filterbank processing module 232R then generates a pre-filtered input signal 233R that is provided to the filterbank 234R. The pre-filtered input signal 233R represents the collective sound signals received at the sound input elements 219R during a given time/analysis frame.

The filterbank 234R uses the pre-filtered input signal 233R to generate a suitable number (i.e., "M") of bandwidth limited "channels," or frequency bins, that each includes a spectral component of the received sound signals that are to be utilized for subsequent sound processing. That is, the filterbank 234R is a plurality of band-pass filters that separates the pre-filtered input signal 233R into multiple components, each one carrying a single frequency sub-band of the original signal (i.e., frequency components of the received sounds signal as included in pre-filtered input signal 233R).

As noted, the channels created by the filterbank 234R are sometimes referred to herein as "sound processing channels," and the sound signal components within each of the sound processing channels are sometimes referred to herein in as band-pass filtered signals or channelized signals. As described further below, the band-pass filtered or channelized signals created by the filterbank 234R may be adjusted/modified as they pass through the right-side sound processing path. As such, the band-pass filtered or channelized signals are referred to differently at different stages of the sound processing path. However, it will be appreciated that reference herein to a band-pass filtered signal or a channelized signal may refer to the spectral component of the received sound signals at any point within the right-side sound processing path (e.g., pre-processed, processed, selected, etc.).

At the output of the filterbank 234R, the channelized signals are initially referred to herein as pre-processed signals 235R. The number of channels (i.e., M) and pre-processed signals 235R generated by the filterbank 234R may depend on a number of different factors including, but not limited to, implant design, number of active electrodes, coding strategy, recipient preference(s), and/or the sound signals themselves. In certain examples, the filterbank 234R may create up to twenty-two (22) channelized signals and the sound processing path is said to include a possible 22 channels (i.e., M equals 22 in this example).

In general, the electrical input signals 231R and the pre-filtered input signal 233R are time domain signals (i.e., processing at pre-filterbank processing module 234R may occur in the time domain). However, the filterbank 234R may operate to deviate from the time domain and, instead, create a "channel" or "channelized" domain in which further sound processing operations are performed. As used herein, the channel domain refers to a signal domain formed by a plurality of amplitudes at various frequency sub-bands. In certain embodiments, the filterbank 234R passes through the amplitude information, but not the phase information, for each of the M channels. This is often due to one or more of the methods of envelope estimation that might be used in each channel, such as half wave rectification (HWR) or low pass filtering (LPF), Quadrature or Hilbert envelope estimation methods among other techniques. As such, the channelized or band-pass filtered signals are sometimes referred to herein as "phase-free" signals. In other embodiments, both the phase and amplitude information may be retained for subsequent processing.

Returning to the example of FIG. 4, as noted the processing module 220R also includes a post-filterbank processing module 236R. The post-filterbank processing module 236R is configured to perform a number of sound processing operations on the pre-processed signals 235R. These sound processing operations include, for example gain adjustments (e.g., multichannel gain control), noise reduction operations, signal enhancement operations (e.g., speech enhancement), etc., in one or more of the channels. As used herein, noise reduction is refers to processing operations that identify the "noise" (i.e., the "unwanted") components of a signal, and then subsequently reduce the presence of these noise components. Signal enhancement refers to processing operations that identify the "target" signals (e.g., speech, music, etc.) and then subsequently increase the presence of these target signal components. Speech enhancement is a particular type of signal enhancement. After performing the sound processing operations, the post-filterbank processing module 236R outputs a plurality of processed channelized signals 237R.

As shown in FIG. 4, the processed channelized signals 237R are provided to the bilaterally-coordinated channel selection module 238R, which is configured to implement the bilaterally-coordinated channel selection techniques presented herein. More specifically, the bilaterally-coordinated channel selection module 238R is configured to select, according to one or more selection rules, which of the M processed channelized signals 237R should selected for stimulation (i.e., selected for presentation at the electrodes). In the embodiments presented herein, the bilaterally-coordinated channel selection module 238R selects a subset N of the M processed channelized signals 237R, but does so using "bilateral sound information." Stated differently, the bilaterally-coordinated channel selection module 238R reduces the sound processing channels from M channels to N channels, using bilateral sound information.

The bilateral sound information is information/data associated with the sound signals received at sound processing unit 203R and information associated with the sound signals received at sound processing unit 203L. At bilaterally-coordinated channel selection module 238R, the information associated with the sound signals received at sound processing unit 203R is obtained at the sound processing unit 203R itself, while the information associated with the sound signals received at sound processing unit 203L is received via the bilateral link 216.

The bilaterally-coordinated channel selection module 238L in the processing module 220L is also configured to select a subset N of the M processed channelized signals 237L using bilateral sound information. At bilaterally-coordinated channel selection module 238L, the information associated with the sound signals received at sound processing unit 203L is obtained at the sound processing unit 203L itself, while the information associated with the sound signals received at sound processing unit 203R is received via the bilateral link 216.

As described further below, the channel selection at each of the bilaterally-coordinated channel selection modules 238R and 238L is "bilateral coordinated," meaning that it is based on the bilateral sound information. However, the bilateral coordination may take a number of different forms and may be implemented in a number of different manners. In certain examples, one of the bilaterally-coordinated channel selection modules 238L or 238R may use the bilateral sound information to select a set of channels (e.g., the N channels or subset of N channels) for use at both of the left and right prostheses and then instruct the other prosthesis regarding which channels to select (e.g., one prosthesis operates as a master device and the second operates as a slave device). In other examples, each of the bilaterally-coordinated channel selection modules 238L and 238R selects N channels using the bilateral sound information and in accordance with a plurality of bilateral channel selection rules. In this example, since the bilateral sound information and bilateral channel selection rules are shared between the two prosthesis, the channels selected by the bilaterally-coordinated channel selection modules 238L and 238R are still bilateral coordinated (i.e., the same N channels or subset of N channels will be selected at each side).

Although FIG. 4 illustrates the bilaterally-coordinated channel selection modules 238L and 238R at each of the sound processing units 203R and 203L, it is to be appreciated that some or all of the channel selection operations may be performed at an external device, such as a mobile computing device (e.g., mobile phone, tablet computer, etc.), remote control, etc., that is in communication with each of the sound processing units 203R and 203L. In such examples, the link 216 may be replaced by, or supplemented by, a link between each of the sound processing units 203R and 203L and the external device. In such examples, the external device comprises a processing module, which in turn includes a bilaterally-coordinated channel selection module. The external device received the bilateral sound information from the sound processing units 203R and 203L, implements the techniques presented herein to use the bilateral sound information to determine the channels for use at the each of the sound processing units 203R and 203L, and then provides the sound processing units 203R and 203L with instructions regarding which channels should be selected. FIG. 3 illustrates an optional external device 207, which includes a processing module 220E, which may be used in such embodiments. That is, in certain embodiments the bilateral cochlear implant system 100 may optionally include external device 207 where the processing module 220E is configured to implement the bilaterally-coordinated channel selection techniques presented herein.

Further details regarding example techniques for using the bilateral sound information to select a set of channels (e.g., select N or a subset of N channels) at a processing module, such as processing module 220R, processing module 220L, and/or processing module 220E, are described further below with reference to FIGS. 5-19C. However, returning first to FIG. 4, the bilaterally-coordinated channel selection module 238R selects N channels. The signals (spectral components) within these channels are referred to as "right-side" or "first" selected signals and are represented in FIG. 4 by arrows 239R. The bilaterally-coordinated channel selection module 238L also selects N channels. The signals (spectral components) within these channels are referred to as "left-side" or "second" selected signals and are represented in FIG. 4 by arrows 239L.

The processing module 220R also comprises the mapping and encoding module 240R. The mapping and encoding module 240R is configured to map the amplitudes of the first selected signals 239R into a set of stimulation commands that represent the attributes of stimulation signals (current signals) that are to be delivered to the recipient so as to evoke perception of the received sound signals. The mapping and encoding module 240R may perform, for example, threshold and comfort level mapping, dynamic range adjustments (e.g., compression), volume adjustments, etc., and may encompass sequential and/or simultaneous stimulation paradigms.

In the embodiment of FIG. 4, the set of stimulation commands that represent the stimulation signals are encoded for transcutaneous transmission (e.g., via an RF link) to the implantable component 210R. This encoding is performed, in the specific example of FIG. 4, at mapping and encoding module 240R. As such, mapping and encoding module 240R operates as an output block configured to convert the plurality of channelized signals into a plurality of output signals 241R. Again, mapping and encoding module 240L operates similarly to mapping and encoding module 240R so as to generate output signals 241L for use by the implantable component 210L.

As noted, FIGS. 5-19C illustrate further details of the bilateral coordination implemented in the bilaterally-coordinated channel selection techniques presented herein. It is to be appreciated that the specific bilateral coordination may depend on an underlying sound processing objective. This sound processing objective could be set, for example, by the recipient, a clinician, an environmental classifier or scene detection algorithm, etc. Described below are six (6) examples of specific bilateral coordination strategies, referred to as bilateral coordination strategies A-F. Strategies A-D propose methods of selecting the same N channels at both the left and right hearing prostheses. Selecting common channels across both hearing prostheses may maximize access to interaural level differences (ILD) cues and may improve the recipient's localization abilities. Strategies E and F propose methods of selecting a set of overlapping channels at both the left and right hearing prostheses, while allowing some channels to be selected independently by each prosthesis. Allowing some channels to be selected independently by each prosthesis may provide a balance between increasing access to ILD cues and presenting sounds that are most dominant on each side. Merely for ease of description, the bilateral coordination strategies A-F will be described with reference to bilateral cochlear implant system 100 of FIGS. 1A-4.

As described elsewhere herein, certain ones of the example bilateral coordination strategies utilize a full audio link between the sound processing units 203R and 203L, where the full sound signals received at each of the left and right hearing prosthesis are used as the bilateral sound information. In these examples, the bilateral link 216 between the left and right hearing prosthesis, or any link with an external device, is of a sufficiently high bandwidth to enable the sharing of the full audio (i.e., the received sound signals) between the prostheses. Other ones of the example bilateral coordination strategies could be implemented using a data link in which the bilateral sound information is data representing one or more attributes of the received sound signals, rather than the full sound signals themselves. The information regarding the received signals shared on the bilateral link may include, for example, maxima, envelope amplitudes, ranked envelope amplitudes, signal-to-noise ratio (SNR) estimates, etc. In these examples, since the full audio is not shared, the bilateral link 216 may be a relative low bandwidth link.

Figure 5:
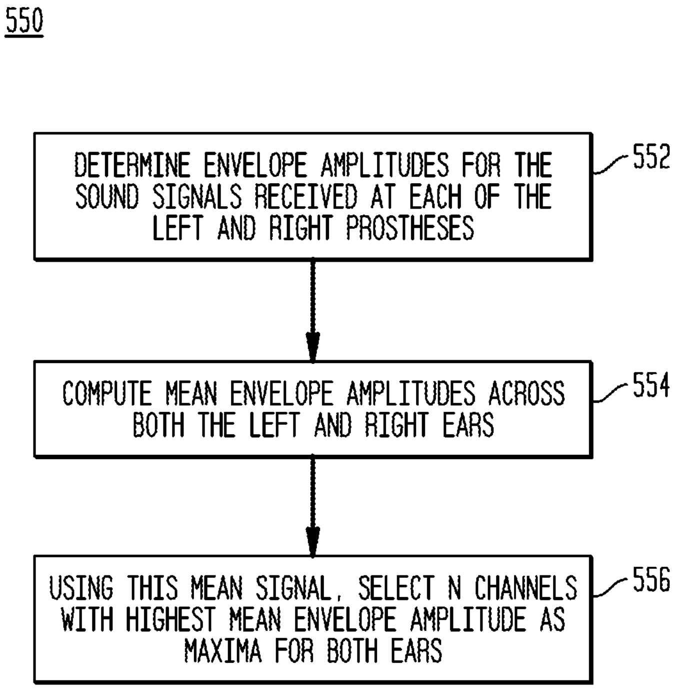
FIG. 5 is a flowchart of a bilaterally-coordinated channel selection method, in accordance with certain embodiments presented herein.

Referring to FIG. 5, shown is a flowchart of an example bilateral coordination method 550 (strategy A) which selects channels corresponding to an overall dominant sound detected by the left and right cochlear implants 102R and 102L. More specifically, method 550 begins at 552 where envelope amplitudes are determined for the sound signals received at each of the sound processing unit 203R and the sound processing unit 203L.

More specifically, each sound processing channel includes a value representing the amplitude of the sound signal envelope within the associated frequency band. The value representing the amplitude of the sound signal envelope is referred to as the "envelope amplitude."

Figure 6A:
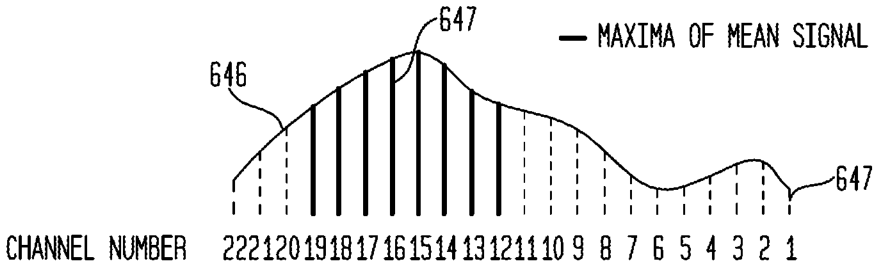
FIGS. 6A-6C are graphs illustrating one example implementation of the bilaterally-coordinated channel selection method of FIG. 5.
Figure 6B:
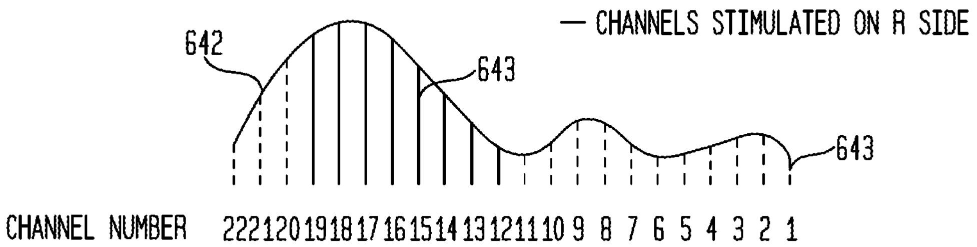
Figure 6C:
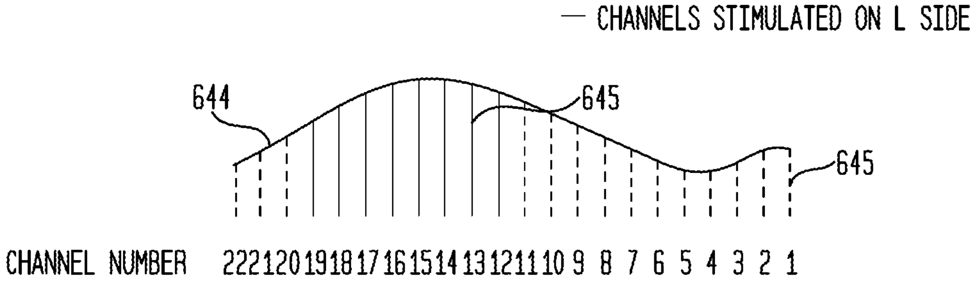

For example, FIG. 6B is a graph illustrating the envelope 642 of the sound signals received at the sound processing unit 203R of bilateral cochlear implant system 100. FIG. 6B also includes lines 643 representing the envelope amplitudes at each of twenty-two (22) sound processing channels. In this example, the sound processing channels are labeled 1-22, with channel 1 being the most basal channel and channel 22 being the most apical channel. FIG. 6C is a graph illustrating the envelope 644 of the sound signals received at the sound processing unit 203L of bilateral cochlear implant system 100. FIG. 6C also includes lines 645 representing the envelope amplitudes at each of twenty-two (22) sound processing channels. Again, the sound processing channels are labeled 1-22, with channel 1 being the most basal channel and channel 22 being the most apical channel.

Returning to FIG. 5, at 554 mean envelope amplitudes (mean signal levels) are computed across both the left and right ears for each sound processing channel. The mean envelope amplitude across both ears refers the mean of the envelope amplitudes at each of the left and right side sound processing units, on the given channel. For example, as noted, FIGS. 6B and 6C illustrate the envelope amplitudes determined at the sound processing unit 203R and the sound processing unit 203L, respectively. FIG. 6A illustrates the mean input envelope amplitudes calculated from the envelope amplitudes shown in FIGS. 6B and 6C. In other words, FIG. 6A illustrates the mean envelope 646 and the mean envelope amplitudes 647 at each of the 22 channels (i.e., the mean of the signals at channel 1 on the left and channel 1 on the right side, the mean of the signals at channel 2 on the left and channel 2 on the right side, and so on).

In certain examples, the mean envelope amplitudes may be calculated as a weighted combination of the left and right side amplitude envelopes so as to control the relative contributions of each side. Equation 1, below, illustrates one example technique for generating a weighted combination of the left and right signals.

$$\text{Mean Signal} = \alpha R + \beta L, \qquad \text{Equation 1:}$$

where R is the right side envelope amplitude for a given channel, L is the left side envelope amplitude for the given channel, and $\alpha$ and $\beta$ are weighting parameters with a constraint that $\alpha$ and $\beta$ sum to a value of 1.

Returning to FIG. 5, at 556 the mean envelope amplitudes across both ears are used to select the N channels having the highest mean envelope amplitudes. These N channels are used by each sound processing units 203R and 203L for further processing (i.e., the N channels having the highest mean envelope amplitudes are selected for use at both ears). In the examples of FIGS. 6A-6C, channels 12-19 are selected for use in stimulating the recipient at both the left and right ears.

Figure 7:
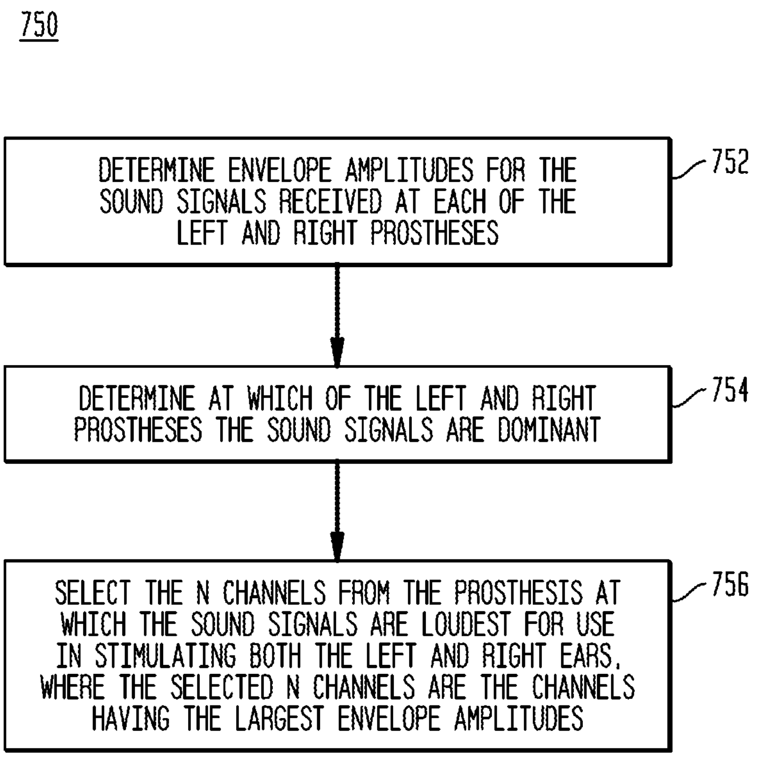
FIG. 7 is a flowchart of a bilaterally-coordinated channel selection method, in accordance with certain embodiments presented herein.

In certain embodiments, preference may be given to sounds arriving from the front by calculating interaural level difference (ILD) for each channel, and penalizing channels with high ILDs. To accomplish this, the channels with the highest weighed amplitude, given as below in Equation 2, would be selected for stimulation.

$$w, w = A - B \cdot |ILD|, \qquad \text{Equation 2:}$$

where A is the mean envelope amplitude, B is a weighting factor relating to the importance of the ILD between the left and right, and |ILD| is the absolute value of the ILD for the given channel Referring next to FIG. 7, shown is a flowchart of an example bilateral coordination method 750 (strategy B) which selects channels corresponding to the dominant ear. More specifically, method 750 begins at 752 where envelope amplitudes are determined for the sound signals received at each of the sound processing unit 203R and the sound processing unit 203L. At 754, a determination is made as which ear the sound signals are dominant. One definition of dominance could be having higher overall input sound pressure levels. However, models of perceived loudness could also be incorporated prior to channel selection. Stated differently, a determination is made as to which of the each sound processing units 203R or 203L received the loudest sounds. For instance, overall loudness could be estimated by either taking the sum or the average of the channel envelopes.

Figure 8A:
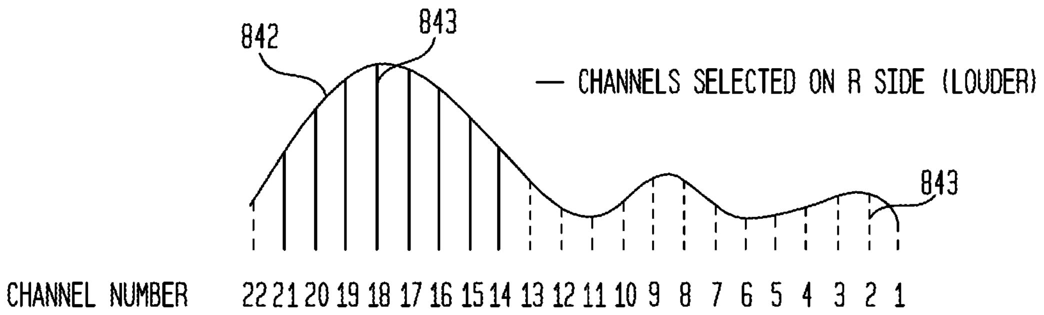
FIGS. 8A and 8B are graphs illustrating one example implementation of the bilaterally-coordinated channel selection method of FIG. 7.
Figure 8B:
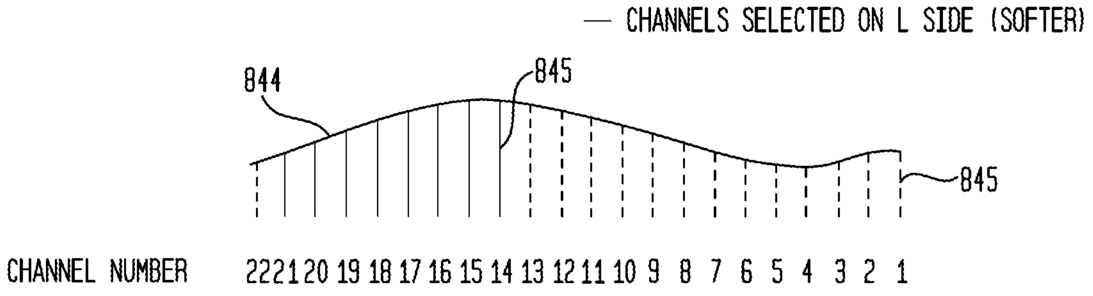

For example, FIG. 8A is a graph illustrating the envelope 842 of sound signals received at sound processing unit 203R of bilateral cochlear implant system 100, as well as the envelope amplitudes 843 determined therefrom and associated channel numbers. FIG. 8B is a graph illustrating the envelope 844 of sound signals received at sound processing unit 203L of bilateral cochlear implant system 100, as well as the envelope amplitudes 845 determined therefrom and associated channel numbers. As shown, the envelope amplitudes 843 at the sound processing unit 203R are, on average, higher than the envelope amplitudes 845 at sound processing unit 203L. As such, in this example, the sound signals received at sound processing unit 203R are louder than those received sound processing unit 203L.

Returning to FIG. 7, at 756, the N channels at the loudest ear having the largest envelope amplitudes are selected as the channels for use in stimulating both the left and right ears. In the examples of FIGS. 8A and 8B, channels 14-21 are selected for use in stimulating both the left and right ears of the recipient.

Figure 9:
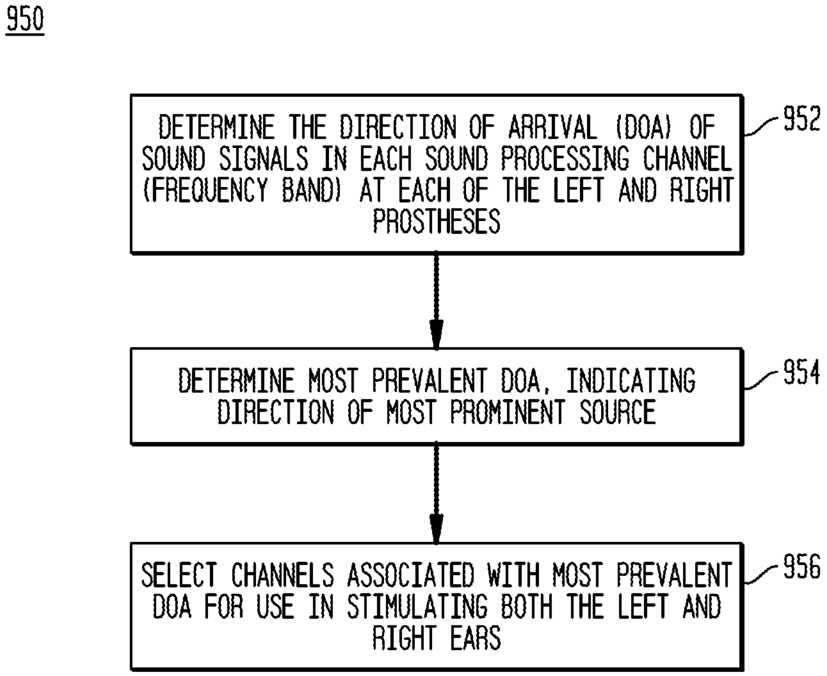
FIG. 9 is a flowchart of a bilaterally-coordinated channel selection method, in accordance with certain embodiments presented herein.

Referring next to FIG. 9, shown is a flowchart of an example bilateral coordination method 950 (strategy C) which selects channels corresponding to the most prominent sound sources. More specifically, method 950 begins at 952 where the direction of arrival (DOA) of the sound signals received at each of the sound processing unit 203R and the sound processing unit 20L is determined. That is, the DOA of the sound components in each frequency band (channel) is determined. For the lower frequencies (i.e. below 1500 Hz), interaural timing differences (ITDs) can be used to obtain a DOA corresponding to each channel. Similarly, for higher frequencies channels (i.e. above 1500 Hz), ILDs can be used to estimate DOAs corresponding to higher frequencies channels (i.e. above 1500 Hz). In certain examples, the ITD/ILD and DOA can be obtained using predetermined mapping functions.

Figure 10A:
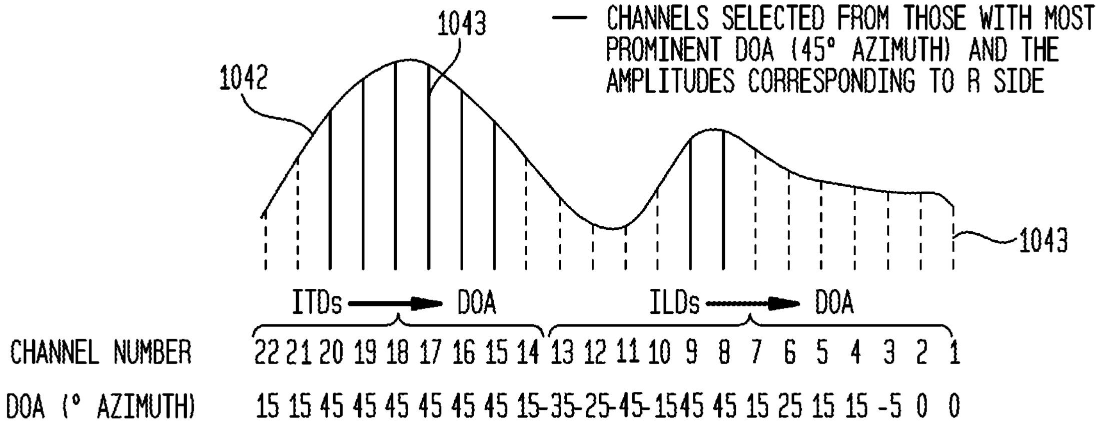
FIGS. 10A and 10B are graphs illustrating one example implementation of the bilaterally-coordinated channel selection method of FIG. 9.
Figure 10B:
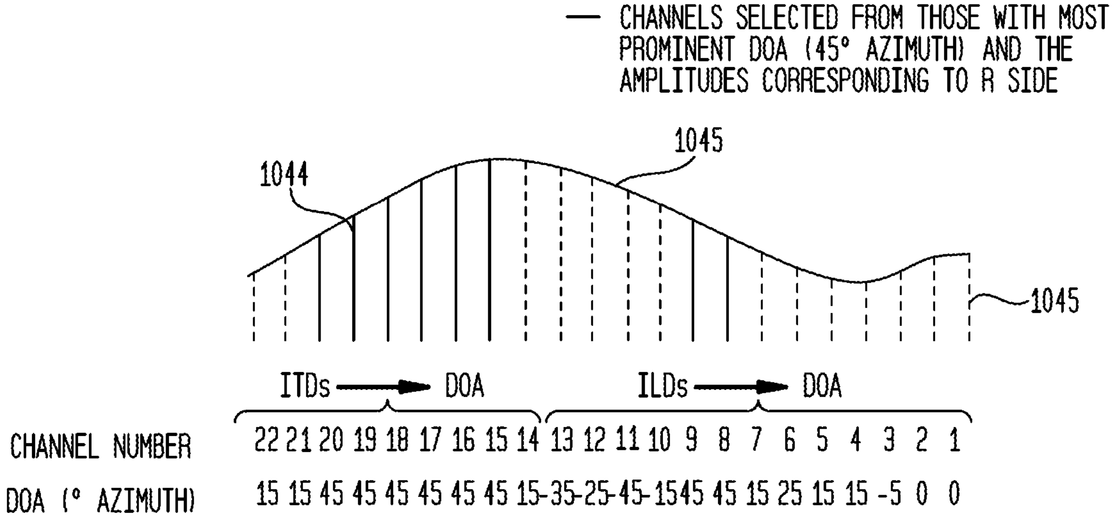

For example, FIG. 10A is a graph illustrating the envelope 942 of sound signals received at sound processing unit 203R of bilateral cochlear implant system 100, as well as the envelope amplitudes 1043 determined therefrom and associated channel numbers. FIG. 10B is a graph illustrating the envelope 1044 of sound signals received at sound processing unit 203L of bilateral cochlear implant system 100, as well as the envelope amplitudes 1045 determined therefrom and associated channel numbers. FIGS. 10A and 10B further each illustrate the determined DOAs for each of the 22 channels (in terms of degrees azimuth). In addition, FIGS. 10A and 10B also each illustrate that, in this example, ILDs are used to determine the DOA for channels 1-13, while ITDs are used to determine the DOA for channels 14-22.

Returning to FIG. 9, at 956, a determination is made as to which DOA is most prevalent (i.e., occurs most) across all channels, indicating the general direction of the most prominent sound source. At 956, the sound processing channels associated with the most prominent sound source are selected for use by the both the sound processing unit 203R and the sound processing unit 203L. The sound processing channels associated with the most prominent sound source may be the channels that have a DOA that is the same as the DOA of the most prominent sound source and/or channels having a DOA within a determined range around the most prominent sound source (e.g., DOAs within 5 degrees, 10 degrees, etc. of the DOA associated with the most prominent sound source). In certain examples, the N channels having a DOA associated with the most prominent source are selected, while the channels with other DOAs are discarded.

In the example of FIGS. 10A and 10B, DOAs between zero (0) and ninety (90) indicate sounds located closest to the sound processing unit 203R (i.e., on the right side of the head), while DOAs between zero (0) and negative ninety (−90) indicate sounds located closest to the sound processing unit 203L (i.e., on the left side of the head). In addition, in the example of FIGS. 10A and 10B, it is determined that a DOA of 45 is most prevalent. As such, it is determined that the sound processing unit 203R is located closed to the most prominent sound source and channels associated with a DOA of 45 are selected as the channels for use in stimulating both the left and right ears. In the examples of FIGS. 10A and 10B, channels 8, 9, and 15-20 are selected for use in stimulating both the left and right ears of the recipient.

In alternative implementation of 956, if there are not N channels with the same DOA, $N_1$ channels could be chosen from the channels with the most prevalent DOA, and $N_2$ channels chosen from the channels with the next most prevalent DOA, $N_3$ maxima from the next most prevalent DOA, and so on, such that $N_1+N_2+N_3 \ldots +N_n=N$, or the total number of desired selected channels.

Strategies A, B, and C, described above with reference to FIGS. 5-10B, are example strategies that utilize a full audio link between the sound processing units 203R and 203L and/or between the sound processing units 203R and 203L and an external device. That is, strategies A, B, and C may rely on the sharing of the received sound signals between the sound processing units 203R and 203L and/or an external device. In contrast, strategies D, E, and F, described below with reference to FIGS. 11-19C illustrate example strategies that utilize a lower bandwidth data link. That is, strategies D, E, and F may not rely on the sharing of the received sound signals between the sound processing units 203R and 203L and/or an external device.

Figure 11:
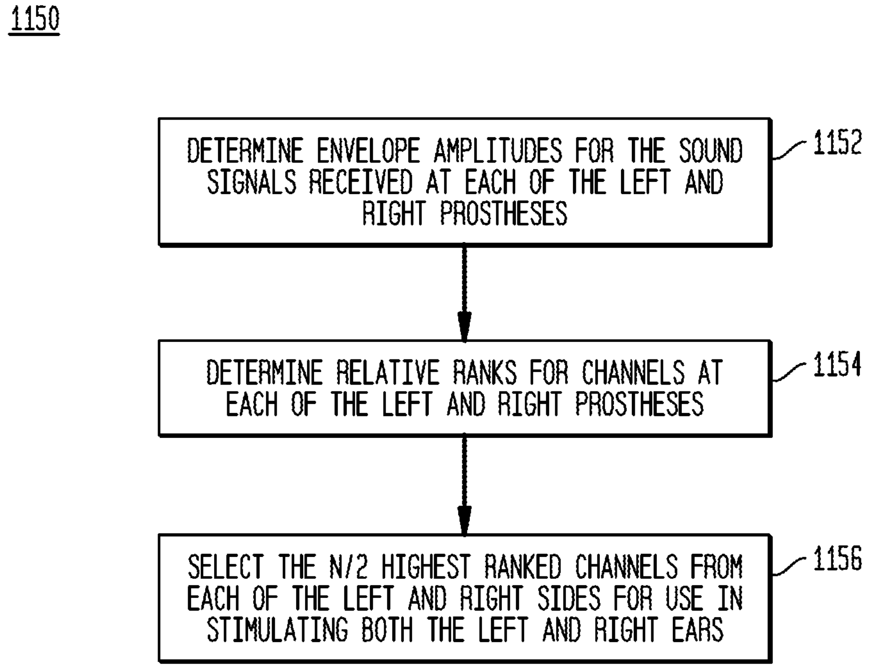
FIG. 11 is a flowchart of a bilaterally-coordinated channel selection method, in accordance with certain embodiments presented herein.

Referring to FIG. 11, shown is a flowchart of an example bilateral coordination method 1150 (strategy D) which selects channels corresponding to dominant sounds in each ear. More specifically, method 1150 begins at 1152 where envelope amplitudes are determined for the sound signals received at each of the sound processing unit 203R and the sound processing unit 203L. At 1154, the channels at each ear are ranked relative to one another based on the envelope amplitudes in each channel (i.e., rank channels from highest to lowest envelope amplitude for each ear).

Figure 12A:
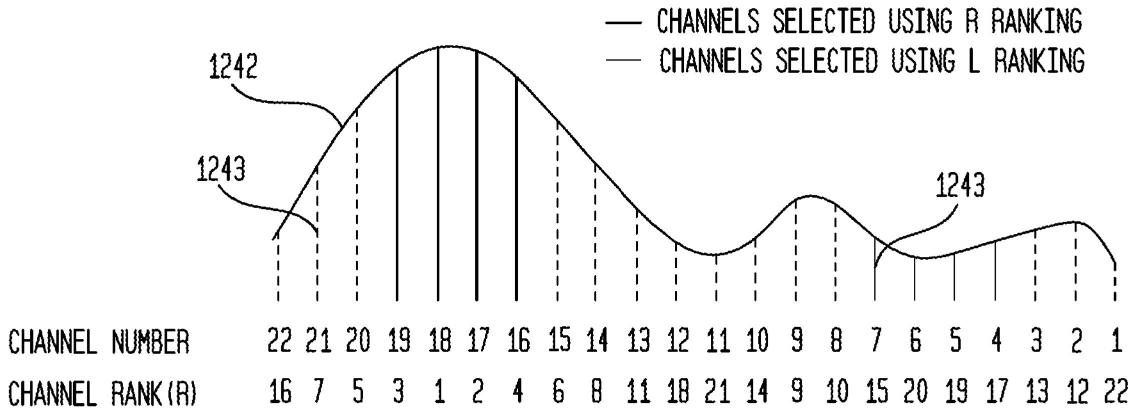
FIGS. 12A and 12B are graphs illustrating one example implementation of the bilaterally-coordinated channel selection method of FIG. 11.
Figure 12B:
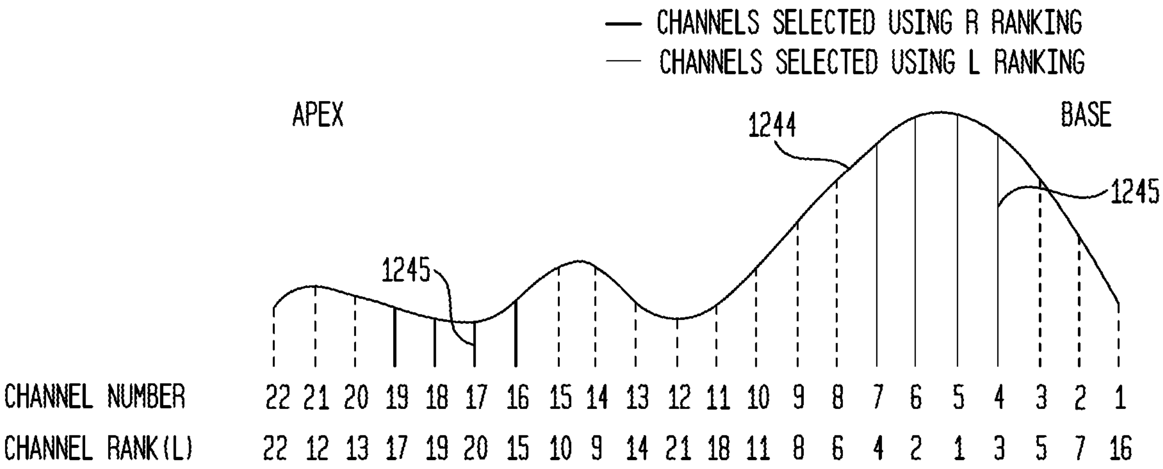

For example, FIG. 12A is a graph illustrating the envelope 1242 of sound signals received at sound processing unit 203R of bilateral cochlear implant system 100, as well as the envelope amplitudes 1243 determined therefrom and associated channel numbers. FIG. 12A also illustrates the relative rankings of these right-side channels, where channel 18 is ranked "1" (i.e., the highest envelope amplitude on the right) and channel 1 is ranked "22" (i.e., the lowest envelope amplitude on the right). FIG. 12B is a graph illustrating the envelope 1244 of sound signals received at sound processing unit 203L of bilateral cochlear implant system 100, as well as the envelope amplitudes 1245 determined therefrom and associated channel numbers. FIG. 12B also illustrates the relative rankings of these left-side channels, where channel 5 is ranked "1" (i.e., the highest envelope amplitude on the left) and channel 22 is ranked "22" (i.e., the lowest envelope amplitude on the left).

Returning to FIG. 11, at 1156, N/2 channels with the highest rank are selected from each ear as the selected channels for both ears. That is, half of the total N channels are selected from the right side, and half of the N total channels are selected from the left side. The channels selected at each side are the N/2 channels at that side having the highest amplitude envelopes (i.e., the channels having a ranking 1 through N/2). The N/2 channels selected at each side are then used to deliver stimulation to both the left and right ears of the recipient.

In certain embodiments, if there are any channels in common between the highest ranked N/2 channels for each ear, the next highest ranked channels across both ears are selected until N channels have been selected. This scenario is illustrated in FIGS. 13A and 13B.

Figure 13A:
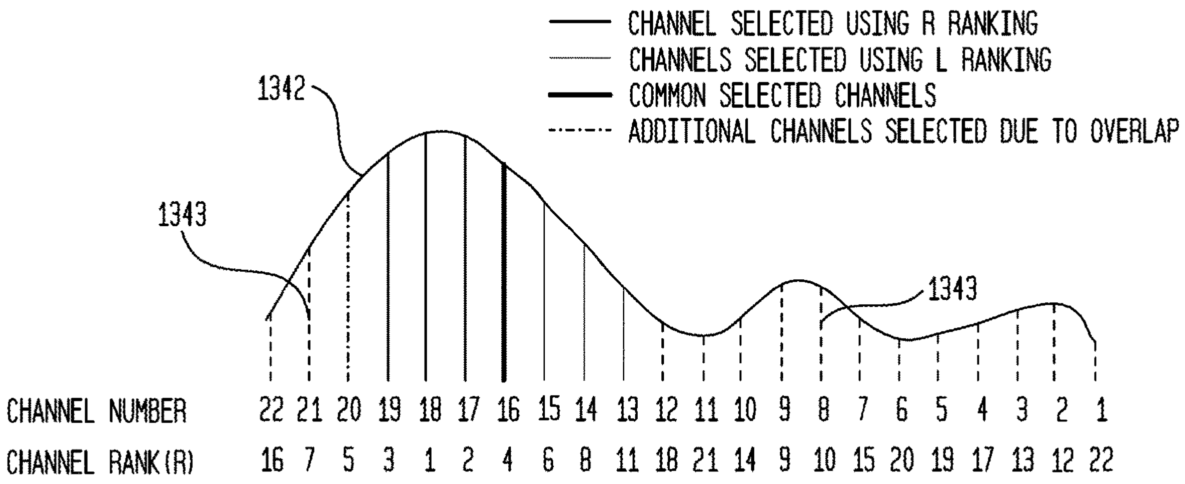
FIGS. 13A and 13B are graphs illustrating an alternative implementation of a bilaterally-coordinated channel selection method of FIG. 11.

More specifically, FIG. 13A is a graph illustrating the envelope 1342 of sound signals received at sound processing unit 203R of bilateral cochlear implant system 100, as well as the envelope amplitudes 1343 determined therefrom and associated channel numbers. FIG. 13A also illustrates the relative rankings of these right-side channels, where channel 18 is ranked "1" (i.e., the highest envelope amplitude on the right) and channel 1 is ranked "22" (i.e., the lowest envelope amplitude on the right). FIG. 13B is a graph illustrating the envelope 1344 of sound signals received at sound processing unit 203L of bilateral cochlear implant system 100, as well as the envelope amplitudes 1345 determined therefrom and associated channel numbers. FIG. 13B also illustrates the relative rankings of these left-side channels, where channel 15 is ranked "1" (i.e., the highest envelope amplitude on the left) and channel 4 is ranked "22" (i.e., the lowest envelope amplitude on the left).

Figure 13B:
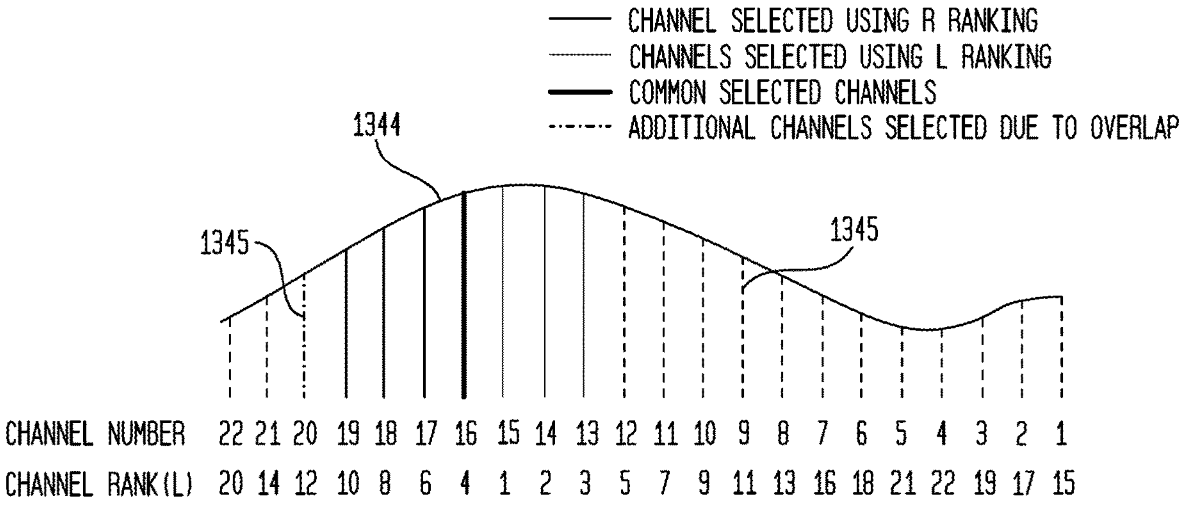

FIGS. 13A and 13B illustrate an example in which eight (8) channels are to be selected for use in stimulating each of the left and right ears of the recipient (i.e., N=8). As such, according to the embodiment of FIG. 11, four (4) channels (i.e., N/2) are to be selected from each of the left and right sides, accordingly to the relative rankings at the respective side. In FIG. 13A, the four highest ranked channels at the right side are channels 18, 17, 19, and 16. In FIG. 13B, the four highest ranked channels at the left side are channels 15, 14, 13, and 16. Therefore, channel 16 is a commonly selected channel and, as result, there is only a total of seven (7) selected channels. In this example, to reach the desired number of eight channels, channel 20 is also selected for use in stimulating the recipient. In other words, in this embodiment, channels 13, 14, 15, 16, 17, 18, 19, and 20 would be selected for use in stimulating both the left and right ears of the recipient.

Figure 14:
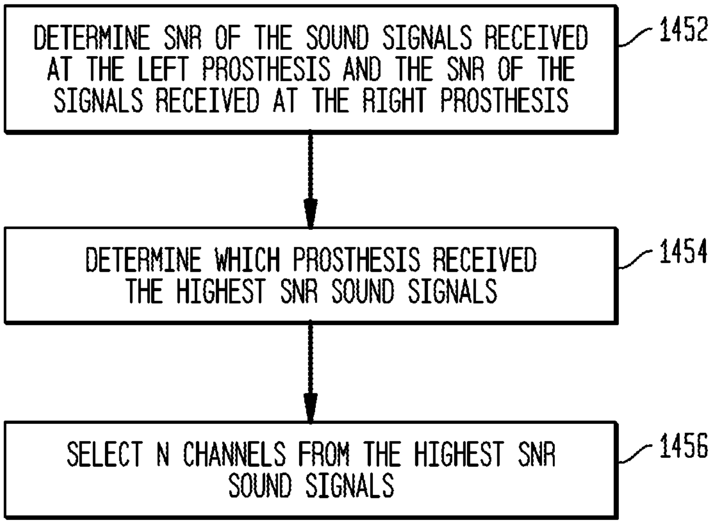
FIG. 14 is a flowchart of a bilaterally-coordinated channel selection method, in accordance with certain embodiments presented herein.

Referring to FIG. 14, shown is a flowchart of an example bilateral coordination method 1450 (strategy E) which selects channels corresponding to the ear with highest signal-to-noise SNR) of the received signals. More specifically, method 1450 begins at 1452 where the SNR of the sound signals received at the sound processing unit 203R is determined, and the where the SNR of the sound signals received at the sound processing unit 203L is determined. The SNR of the received signals may be determined in a number of different manners. For example, the system could calculate a channel-by-channel SNR for certain denoising strategies, and could use the average SNR across channel. Alternatively, the SNR could be calculated for the input signal (before channelizing).

At 1454, a determination is made as to which of the sound processing unit 203R or the sound processing unit 203L received sound signals having the highest SNR. This could be determined by either calculating the SNR of the input signal, or by calculating the average of the channel-specific SNR for each device. At 1456, the N channels are selected from the side at which the sound signals have the highest SNR, and these same channels are then used for stimulation at the other ear. The N selected channels are the N channels having the highest envelope amplitudes.

Figure 15A:
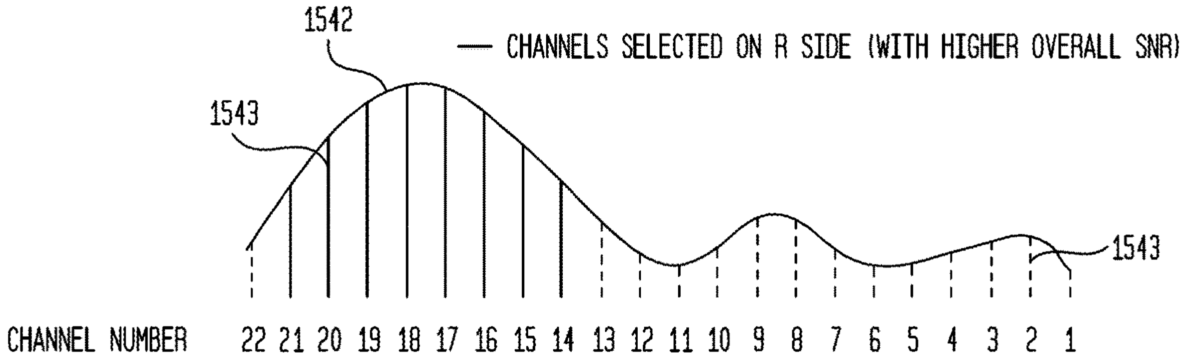
FIGS. 15A and 15B are graphs illustrating one example implementation of the bilaterally-coordinated channel selection method of FIG. 14.
Figure 15B:
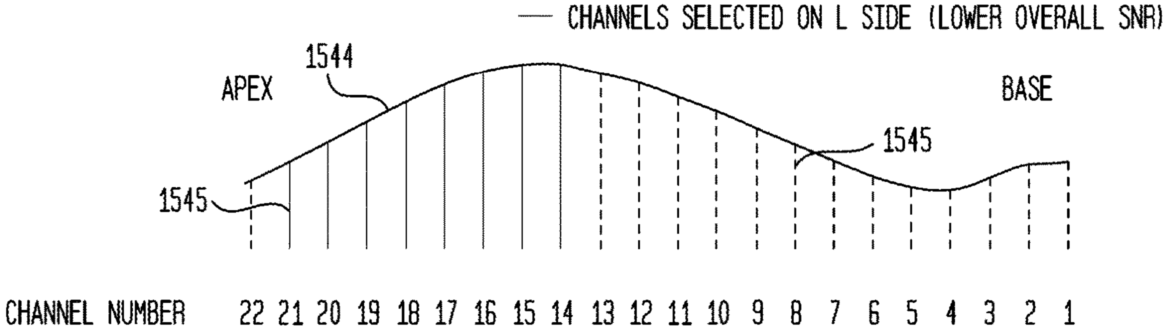

For example, FIG. 15A is a graph illustrating the envelope 1542 of sound signals received at sound processing unit 203R of bilateral cochlear implant system 100, as well as the envelope amplitudes 1543 determined therefrom and associated channel numbers. FIG. 15B is a graph illustrating the envelope 1544 of sound signals received at sound processing unit 203L of bilateral cochlear implant system 100, as well as the envelope amplitudes 1545 determined therefrom and associated channel numbers. In the example of FIGS. 15A and 15B, the sound signals received at sound processing unit 203R have the highest SNR and, as such, the N channels having the highest envelope amplitudes at sound processing unit 203R are the channels selected for use by both sound processing units 203R and 203L. In the particular example of FIGS. 15A and 15B, channels 14-21 are selected for use at both the left and right sides.

As noted, FIGS. 14, 15A, and 15B illustrate examples in which N channels are selected from the side at which the sound signals have the highest SNR. In an alternative embodiment, N/2 channels could be selected from the side at which the sound signals have the highest SNR and then also used at the contralateral sound processing unit. However, the remaining N/2 channels could be independently selected at each of the sound processing units 203R and 203L.

Figure 16A:
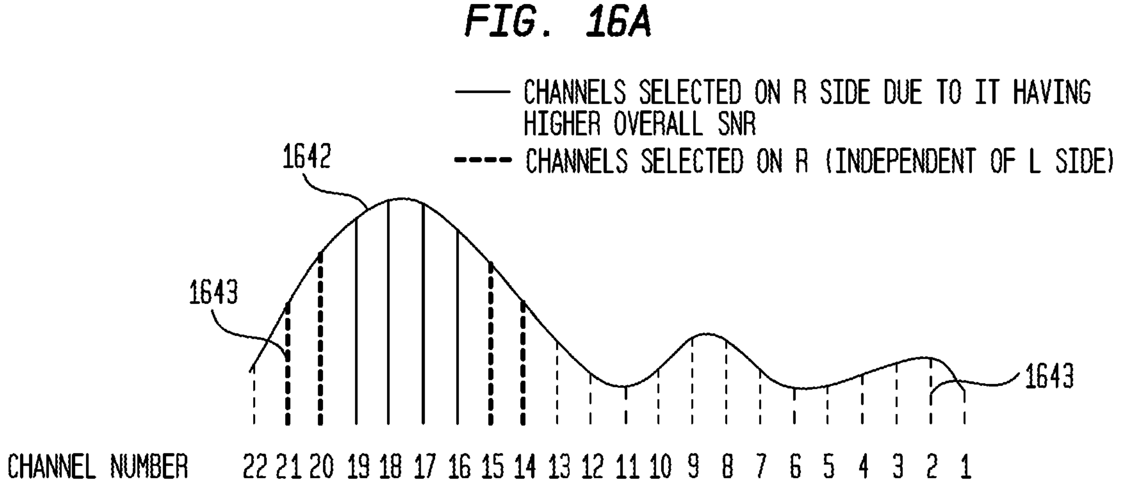
FIGS. 16A and 16B are graphs illustrating an alternative implementation of a bilaterally-coordinated channel selection method of FIG. 14.
Figure 16B:
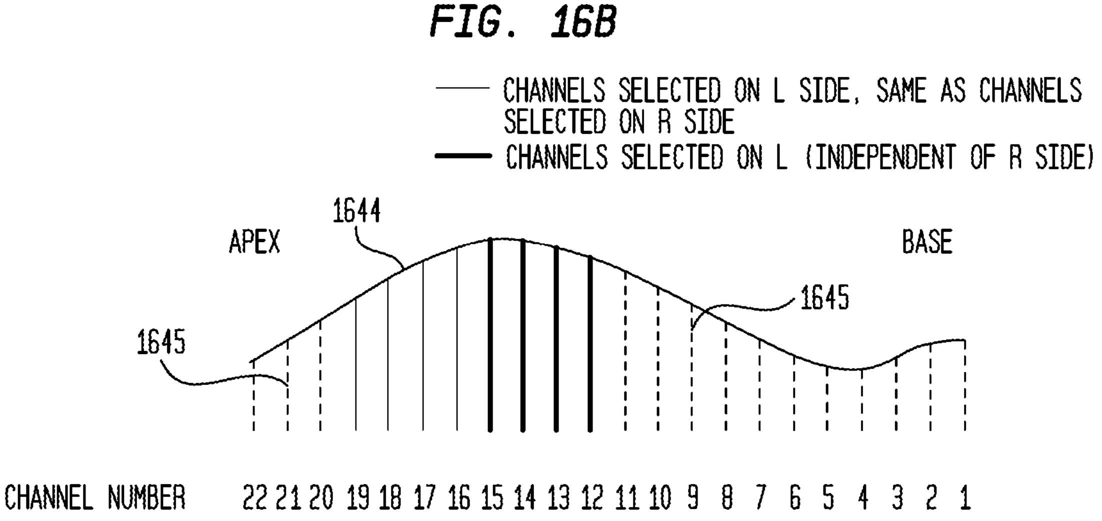

For example, FIG. 16A is a graph illustrating the envelope 1642 of sound signals received at sound processing unit 203R of bilateral cochlear implant system 100, as well as the envelope amplitudes 1643 determined therefrom and associated channel numbers. FIG. 16B is a graph illustrating the envelope 1644 of sound signals received at sound processing unit 203L of bilateral cochlear implant system 100, as well as the envelope amplitudes 1645 determined therefrom and associated channel numbers.

In the example of FIGS. 16A and 16B, the sound signals received at sound processing unit 203R have the highest SNR and, as such, the N/2 channels having the highest envelope amplitudes at sound processing unit 203R are the channels selected for use by both sound processing units 203R and 203L. In the particular example of FIGS. 16A and 16B, N=8 and channels 16-19 are selected for use at both the left and right sides (i.e., channels 16-19 are the four channels at sound processing unit 203R having the highest envelope amplitudes). As noted, sound processing units 203R and 203L are able to independently select the remaining N/2 (i.e., 4) channels used subsequent processing at the respective sound processing unit and, accordingly, used for stimulating the right and left ears, respectively, of the recipient. FIG. 16A illustrates at channels 14, 15, 20, and 21 are additionally selected at sound processing unit 203R, while FIG. 16B illustrates that channels 12, 13, 14, and 15 are additionally selected at sound processing unit 203L. In other words, the right ear of the recipient is stimulated using channels 14-21, while the left ear of the recipient is stimulated using channels 12-19.

Figure 17:
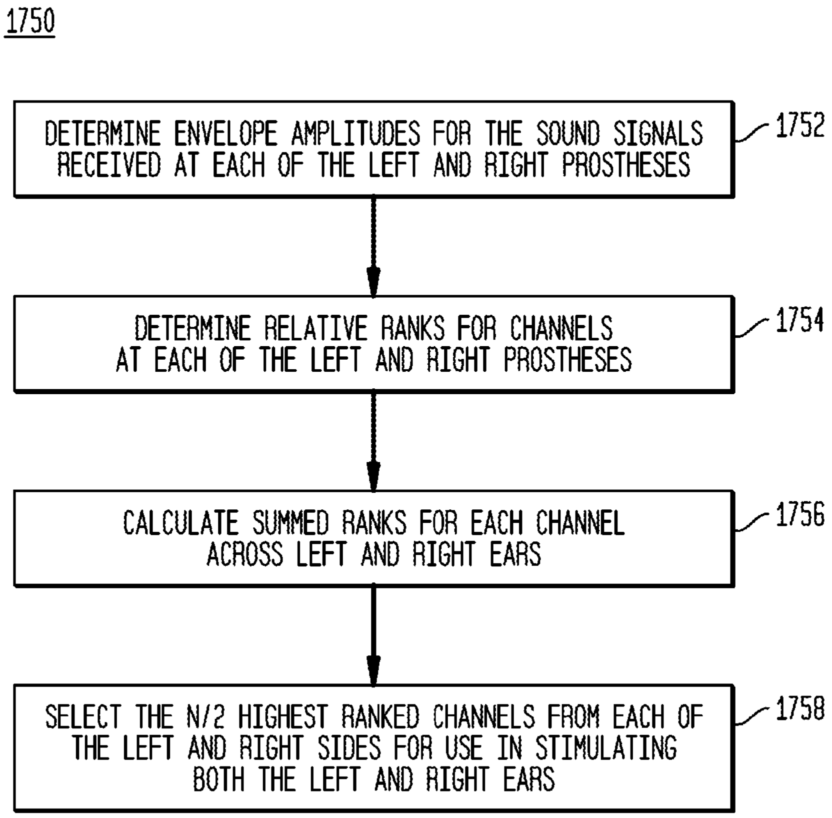
FIG. 17 is a flowchart of a bilaterally-coordinated channel selection method, in accordance with certain embodiments presented herein.

Referring next to FIG. 17, shown is a flowchart of an example bilateral coordination method 1450 (strategy E) which selects channels with the highest summed envelope rank across both ears. More specifically, method 1750 begins at 1752 where envelope amplitudes are determined for the sound signals received at each of the sound processing unit 203R and the sound processing unit 203L. At 1754, the channels at each ear are ranked relative to one another based on the envelope amplitudes in each channel (i.e., rank channels from highest to lowest envelope amplitude for each ear). At 1756, a summed channel envelope rank across both the left and right ears is computed. That is, the individual relative ranks for a given channel at each of the sound processing units 203R and 203L are added together (i.e., the envelope amplitude of channel 1 at the sound processing unit 203R is added to the envelope amplitude of channel 1 at the sound processing unit 203L, envelope amplitude of channel 2 at the sound processing unit 203R is added to the envelope amplitude of channel 2 at the sound processing unit 203L, and so on).

For example, FIG. 18A is a graph illustrating the envelope 1842 of sound signals received at sound processing unit 203R of bilateral cochlear implant system 100, as well as the envelope amplitudes 1843 determined therefrom and associated channel numbers. FIG. 18A also illustrates the relative rankings of these right-side channels, where channel 18 is ranked “1” (i.e., the highest envelope amplitude on the right) and channel 1 is ranked “22” (i.e., the lowest envelope amplitude on the right). FIG. 18B is a graph illustrating the envelope 1844 of sound signals received at sound processing unit 203L of bilateral cochlear implant system 100, as well as the envelope amplitudes 1845 determined therefrom and associated channel numbers. FIG. 18B also illustrates the relative rankings of these left-side channels, where channel 15 is ranked “1” (i.e., the highest envelope amplitude on the left) and channel 4 is ranked “22” (i.e., the lowest envelope amplitude on the left).

FIG. 18C is a diagram illustrating the summed channel envelope ranks for the example of FIGS. 18A and 18B, along with the associated channel numbers. In this example, channel 15 has the highest summed channel envelope rank (i.e., the lowest combined total of the left and right side ranks from FIGS. 18A and 18B). Conversely, channel 5 has the lowest summed channel envelope rank (i.e., the highest combined total of the left and right side ranks from FIGS. 18A and 18B).

Returning to FIG. 17, at 1756, the N channels with the highest summed channel envelope rank are selected and then used for use by both sound processing units 203R and 203L. In the particular example of FIGS. 18A and 18B, channels 13-20 are selected for use at both the left and right sides.

As noted, FIGS. 17, 18A, and 18B illustrate examples in which the N channels having the highest summed channel envelope rank are selected for use by both of the sound processing units 203R and 203L. In an alternative embodiment, N/2 channels having the highest summed channel envelope rank are selected for use by both of the sound processing units 203R and 203L. However, the remaining N/2 channels could be independently selected at each of the sound processing units 203R and 203L. For example, each sound processing units 203R and 203L could pick the next highest ranked N/2 channels, as ranked at the respective side, that have not already been selected using the highest summed channel envelope rank.

For example, FIG. 19A is a graph illustrating the envelope 1942 of sound signals received at sound processing unit 203R of bilateral cochlear implant system 100, as well as the envelope amplitudes 1943 determined therefrom and associated channel numbers. FIG. 19A also illustrates the relative rankings of these right-side channels, where channel 18 is ranked “1” (i.e., the highest envelope amplitude on the right) and channel 1 is ranked “22” (i.e., the lowest envelope amplitude on the right). FIG. 19B is a graph illustrating the envelope 1944 of sound signals received at sound processing unit 203L of bilateral cochlear implant system 100, as well as the envelope amplitudes 1945 determined therefrom and associated channel numbers. FIG. 19B also illustrates the relative rankings of these left-side channels, where channel 5 is ranked "1" (i.e., the highest envelope amplitude on the left) and channel 12 is ranked "22" (i.e., the lowest envelope amplitude on the left).

FIG. 19C is a diagram illustrating the summed channel envelope ranks for the example of FIGS. 19A and 19B, along with the associated channel numbers. In this example, channels 8 and 15 have the highest summed channel envelope rank (i.e., the lowest combined total of the left and right side ranks from FIGS. 19A and 19B), while channels 9 and 14 have second highest summed channel envelope rank. In the particular example of FIGS. 19A and 19B, N=8 and channels 8, 9, 14, and 15 are selected for use at both the left and right sides. As noted, sound processing units 203R and 203L are able to independently select the remaining N/2 (i.e., 4) channels used subsequent processing at the respective sound processing unit and, accordingly, used for stimulating the right and left ears, respectively, of the recipient. FIG. 19A illustrates that channels 16-19 are additionally selected at sound processing unit 203R, while FIG. 19B illustrates that channels 4-7 are additionally selected at sound processing unit 203L. In other words, the right ear of the recipient is stimulated using channels 8, 9, and 14-19, while the left ear of the recipient is stimulated using channels 4-9, 14, and 15.

Figure 20:
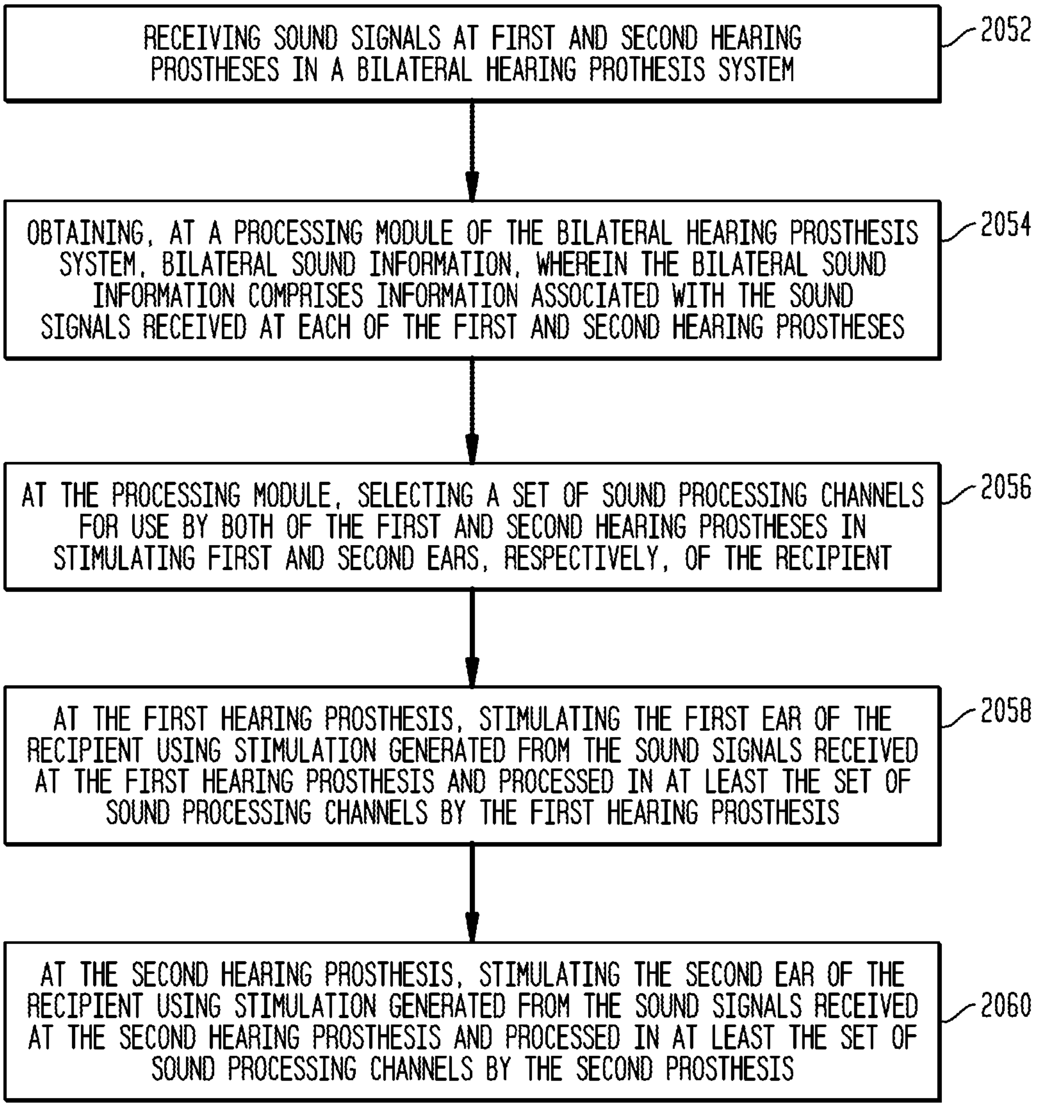
FIG. 20 is flowchart of a method, in accordance with embodiments presented herein.

FIG. 20 is a flowchart illustrating a method 2050 in accordance with certain embodiments presented herein. Method 2050 begins at 2052 where sound signals are received at first and second hearing prostheses in a bilateral hearing prosthesis system. At 2054, a processing module of the bilateral hearing prosthesis system obtains bilateral sound information. The bilateral sound information comprises information associated with the sound signals received at each of the first and second hearing prostheses. At 2056, the processing module selects a set of sound processing channels for use by both of the first and second hearing prostheses in stimulating first and second ears, respectively, of the recipient. At 2058, the first hearing prosthesis stimulates the first ear of the recipient using stimulation generated from the sound signals received at the first hearing prosthesis and processed in at least the set of sound processing channels by the first hearing prosthesis. At 2060, the second hearing prosthesis, stimulating the second ear of the recipient using stimulation generated from the sound signals received at the second hearing prosthesis and processed in at least the set of sound processing channels by the second hearing prosthesis.

Described above are various methods for bilaterally-coordinating channel selection in a bilateral hearing prosthesis system. The above described methods are not mutually exclusive and instead may be combined with one another in various arrangements. In additional, further enhancements may be used in the above methods. For example, if the number of selected channels, N, is greater than half of the number of total channels (i.e., greater N>M/2), then the techniques described above may only share the excluded channels instead of the selected channels.

In other examples, the bilateral prostheses may only coordinate the channel selection in certain frequency ranges (i.e., only in the high frequency channels). For example, the mismatch in channel selection may be highest for higher frequency regions due to the larger effect of head shadow, so an alternate embodiment would only share data and enforce channel selection only for higher frequencies.

Additionally, the techniques presented herein may not share the bilateral sound information for every time/analysis window. The bilateral sound information may not need be shared for every time window due to, for example, binaural cues averaging over time. In certain embodiments, knowledge of matched electrodes across sides may be utilized. In particular, if the perceptual pairing of electrodes across sides is known (i.e., in pitch, position, smallest ITD), then this information could supersede pairing determined by electrode number.

Moreover, it may be possible to match electrode regions rather than individual electrodes across sides. For example, the implanted electrode arrays could be divided into regions, and the coordinated strategy could ensure that the stimulated regions, rather than individual electrodes, are matched across the left and right sides.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:

receiving sound signals at first and second hearing devices in a bilateral hearing device system configured to be worn by a recipient;

obtaining, at a processing module, bilateral sound information, wherein the bilateral sound information comprises a first set of sound information associated with the sound signals received at the first hearing device and a second set of sound information associated with the sound signals received at the second hearing device;

at the processing module, selecting, based on the bilateral sound information, a set of sound processing channels for use by both of the first and second hearing devices in stimulating first and second ears, respectively, of the recipient;

at the first hearing device, stimulating the first ear of the recipient using stimulation generated from the sound signals received at the first hearing device and processed in at least the set of sound processing channels by the first hearing device; and at the second hearing device, stimulating the second ear of the recipient using stimulation generated from the sound signals received at the second hearing device and processed in at least the set of sound processing channels by the second hearing device.

2. The method of claim 1, wherein the first and second hearing devices are configured to stimulate the first and second ears of the recipient, respectively, each using sound signals processed in a specified number of sound processing channels, and wherein selecting the set of sound processing channels for use by both of the first and second hearing devices comprises:

selecting, at the processing module, only a first subset of the specified number of sound processing channels for use by both of the first and second hearing devices in stimulating first and second ears, respectively, of the recipient.

3. The method of claim 2, further comprising:

independently selecting, at the first hearing device, a second subset of the specified number of sound processing channels for use in stimulating the first ear of the recipient; and independently selecting, at the second hearing device, a second subset of the specified number of sound processing channels for use in stimulating the second ear of the recipient.

4. The method of claim 1, wherein the processing module is disposed in the first hearing device, and wherein obtaining the bilateral sound information includes:

generating the first set of sound information from the sound signals received at the first hearing device; and wirelessly receiving, at the first hearing device, the second set of sound information from the second hearing device, wherein the second set of sound information is generated by the second hearing device based on the sound signals received at the second hearing device.

5. The method of claim 4, wherein the set of sound processing channels for use by both of the first and second hearing devices in stimulating first and second ears, respectively, of the recipient is selected at the first hearing device, and wherein the method comprises:

sending, from the first hearing device to the second hearing device, an indication of the set of sound processing channels for use by second hearing device.

6. The method of claim 1, wherein the processing module is disposed in each of the first hearing device and the second hearing device, and wherein obtaining the bilateral sound information includes:

at the first hearing device:

generating the first set of sound information from the sound signals received at the first hearing device;

wirelessly receiving the second set of sound information from the second hearing device;

at the second hearing device:

generating the second set of sound information from the sound signals received at the second hearing device; and wirelessly receiving the first set of sound information from the first hearing device, wherein the second set of sound information is generated by the second hearing device based on the sound signals received at the second hearing device.

7. The method of claim 1, wherein the processing module is disposed in an external device that is separate from each of the first and second hearing devices, and wherein obtaining the bilateral sound information includes:

wirelessly receiving, at the external device, the first set of sound information from the first hearing device; and wirelessly receiving, at the external device, the second set of sound information from the second hearing device.

8. The method of claim 1, wherein the bilateral sound information comprises the sound signals received at the first and second hearing devices.

9. The method of claim 1, wherein the bilateral sound information comprises data representing one or more attributes of the sound signals received at the first and second hearing devices.

10. The method of claim 1, wherein selecting, based on the bilateral sound information, a set of sound processing channels for use by both of the first and second hearing devices in stimulating first and second ears, respectively, of the recipient, comprises:

determining a plurality of envelope amplitudes for the sound signals received at each of the first and second hearing devices, wherein each of the plurality of envelope amplitudes corresponds to one of a plurality of sound processing channels at each of the first and second hearing devices;

calculating mean envelope amplitudes across both the first and second hearing devices for each of the plurality of sound processing channels; and using the mean envelope amplitudes across both the first and second hearing devices to select the set of sound processing channels for use by both of the first and second hearing devices.

11. The method of claim 10, wherein using the mean envelope amplitudes across both the first and second hearing devices to select the set of sound processing channels for use by both of the first and second hearing devices comprises:

using the mean envelope amplitudes to select a set of N channels having a highest mean envelope of amplitudes across both the first and second hearing devices.

12. The method of claim 10, wherein calculating the mean envelope amplitudes across both the first and second hearing devices for each of the plurality of sound processing channels comprises:

calculating a weighted combination of the envelope amplitudes determined at each of the first and second hearing devices for the corresponding one of the plurality of sound processing channels.

13. The method of claim 1, wherein, based on the bilateral sound information, selecting the set of sound processing channels for use by both of the first and second hearing devices in stimulating first and second ears, respectively, of the recipient, comprises:

determining a plurality of envelope amplitudes for the sound signals received at each of the first and second hearing devices, wherein each of the plurality of envelope amplitudes corresponds to one of a plurality of sound processing channels at each of the first and second hearing devices;

determining, using the envelope amplitudes, which of the first or second hearing devices received louder sound signals; and selecting the set of the sound processing channels from the sound processing channels at the one of the first or second hearing devices that received the louder sound signals.

14. The method of claim 1, wherein selecting, based on the bilateral sound information, the set of sound processing channels for use by both of the first and second hearing devices in stimulating first and second ears, respectively, of the recipient, comprises:

determining a direction of arrival (DOA) for components of the sound signals received by the first and second hearing devices, where each DOA is associated with one of a plurality of sound processing channels at each of the first and second hearing devices;

determining a most prevalent DOA for the components of the sound signals; and selecting, as the set of the sound processing channels, one or more channels associated with most prevalent DOA for the components of the sound signals.

15. The method of claim 1, wherein, based on the bilateral sound information, selecting the set of sound processing channels for use by both of the first and second hearing devices in stimulating first and second ears, respectively, of the recipient, comprises:

determining a plurality of envelope amplitudes for the sound signals received at each of the first and second hearing devices, wherein each of the plurality of envelope amplitudes corresponds to one of a plurality of sound processing channels at each of the first and second hearing devices;

determining relative ranks for the plurality of envelope amplitudes, wherein the relative ranks are determined with reference to other envelope amplitudes at the same one of the first or second hearing devices; and selecting the set of the sound processing channels based on the relative ranks for the plurality of envelope amplitudes.

16. The method of claim 15, wherein selecting the set of the sound processing channels based on the relative ranks for the plurality of envelope amplitudes determined at each of the first and second hearing devices, comprises:

selecting, as a first subset of the channels in the set of the sound processing channels, sound processing channels having a highest relative ranks at the first hearing device; and selecting, as a second subset of the channels in the set of the sound processing channels, sound processing channels having the highest relative ranks at the second hearing device.

17. The method of claim 15, wherein selecting the set of the sound processing channels based on the relative ranks for the plurality of envelope amplitudes determined at each of the first and second hearing devices, comprises:

summing the relative ranks across both the first and second hearing devices to generate a set of summed envelope ranks; and selecting the set of the sound processing channels based on the summed envelope ranks.

18. The method of claim 1, wherein selecting, based on the bilateral sound information, the set of sound processing channels for use by both of the first and second hearing devices in stimulating first and second ears, respectively, of the recipient, comprises:

determining signal to noise ratios (SNRs) for the sound signals received at each of the first and second hearing devices, respectively;

determining which of the first or second hearing devices received sound signals with a highest SNR; and selecting the set of the sound processing channels from the sound processing channels at the one of the first or second hearing devices that received the sound signals with the highest SNR.

19. The method of claim 1, wherein selecting, based on the bilateral sound information, a set of sound processing channels for use by both of the first and second hearing devices in stimulating first and second ears, respectively, of the recipient, comprises:

selecting, based on the bilateral sound information, a first subset of channels associated with the first hearing device;

selecting, based on the bilateral sound information, a second subset of channels associated with the second hearing device, wherein the first subset of channels is different from the second subset of channels; and providing the first subset of channels and the second subset of channels as the set of sound processing channels for use by both of the first and second hearing devices.

20. A method, comprising:

receiving sound signals at a first hearing device in a bilateral hearing device system, wherein the first hearing device is located at a first ear of a recipient;

processing the sound signals in a plurality of sound processing channels;

sending information associated with the sound signals received at the first hearing device to a processing module;

receiving, from the processing module, an indication of a subset of the plurality of sound processing channels for use in stimulating the first ear of the recipient;

selecting, at the processing module, the subset of the plurality of sound processing channels for use at the first hearing device based on the information associated with the sound signals received at the first hearing device and information associated with the sound signals received at a second hearing device in the bilateral hearing device system; and stimulating the first ear of the recipient using stimulation generated from the sound signals received at the first hearing device and processed in at least the subset of the plurality of sound processing channels.

21. The method of claim 20, wherein the first hearing device is configured to stimulate the first ear of the recipient using sound signals processed in a specified number of sound processing channels, and wherein selecting the subset of the plurality of sound processing channels for use by the first hearing device comprises:

selecting, at the processing module, all of the specified number of sound processing channels for use by the first hearing device in stimulating the first ear of the recipient.

22. The method of claim 20, wherein the first hearing device is configured to stimulate the first ear of the recipient using sound signals processed in a specified number of sound processing channels, and wherein selecting the subset of the plurality of sound processing channels for use by the first hearing device comprises:

selecting, at the processing module, only a first subset of the specified number of sound processing channels for use by the first hearing device in stimulating the first ear of the recipient.

23. The method of claim 22, further comprising:

independently selecting, at the first hearing device, a second subset of the specified number of sound processing channels for use in stimulating the first ear of the recipient.

24. The method of claim 20, wherein sending information associated with the sound signals received at the first hearing device to the processing module comprises:

sending data representing one or more attributes of the sound signals received at the first hearing device to the processing module.

25. The method of claim 20, wherein sending information associated with the sound signals received at the first hearing device to the processing module comprises:

sending the sound signals received at the first hearing device to the processing module.

26. One or more non-transitory computer readable storage media comprising instructions that, when executed by one or more processors in a bilateral hearing device system comprising first and second hearing devices, cause the or more processors to:

obtain bilateral sound information, wherein the bilateral sound information comprises a first set of sound information associated with the sound signals received at a first hearing device of the bilateral hearing device system and a second set of sound information associated with the sound signals received at a second hearing device of the bilateral hearing device system;

determine a set of sound processing channels for use by both of the first and second hearing devices in stimulating first and second ears, respectively, of the recipient; and initiate delivery of stimulation signals to the first ear of the recipient using stimulation signals generated from the sound signals received at the first hearing device and processed in at least the set of sound processing channels by the first hearing device.

27. The one or more non-transitory computer readable storage media of claim 26, wherein the first and second hearing devices are configured to stimulate the first and second ears of the recipient, respectively, each using sound signals processed in a specified number of sound processing channels, and wherein the instructions operable to determine the set of sound processing channels for use by both of the first and second hearing devices comprise instructions operable to:

determine only a first subset of the specified number of sound processing channels for use by both of the first and second hearing devices in stimulating first and second ears, respectively, of the recipient.

28. The one or more non-transitory computer readable storage media of claim 27, further comprising instructions operable to:

independently select, at the first hearing device, a second subset of the specified number of sound processing channels for use in stimulating the first ear of the recipient.

29. The one or more non-transitory computer readable storage media of claim 26, wherein the instructions operable to obtain the bilateral sound information comprise instructions operable to:

generate first set of sound information from the sound signals received at the first hearing device; and wirelessly receive a second set of sound information from the second hearing device, wherein the second set of sound information is generated by the second hearing device based on the sound signals received at the second hearing device.

* * * * *